US012629376B2

(12) United States Patent
Skorecki et al.

(10) Patent No.: US 12,629,376 B2
(45) Date of Patent: May 19, 2026

(54) COMPOSITION FOR USE IN THE TREATMENT OF ApoL1-ASSOCIATED DISEASE

(71) Applicants: RAMBAM MED-TECH LTD., Haifa (IL); TECHNION RESEARCH & DEVELOPMENT FOUNDATION LIMITED, Haifa (IL)

(72) Inventors: Karl Skorecki, Zefat (IL); Ira Bavli-Kertselli, Kiryat Ata (IL); Tali Shemer, Haifa (IL); Etty Kruzel-Davila, Haifa (IL); Orly Tabachnikov, Haifa (IL)

(73) Assignee: Vertex Pharmaceuticals Incorporated, Boston, MA (US)

( * ) Notice: Subject to any disclaimer, the term of this patent is extended or adjusted under 35 U.S.C. 154(b) by 643 days.

(21) Appl. No.: 17/923,508

(22) PCT Filed: May 6, 2021

(86) PCT No.: PCT/IL2021/050521

§ 371 (c)(1),
(2) Date: Nov. 4, 2022

(87) PCT Pub. No.: WO2021/224927

PCT Pub. Date: Nov. 11, 2021

(65) Prior Publication Data

US 2023/0201201 A1 Jun. 29, 2023

Related U.S. Application Data

(60) Provisional application No. 63/021,222, filed on May 7, 2020.

(51) Int. Cl.
*A61K 31/517* (2006.01)
*A61K 31/454* (2006.01)

(52) U.S. Cl.
CPC .......... *A61K 31/517* (2013.01); *A61K 31/454* (2013.01)

(58) Field of Classification Search
CPC .... A61K 31/517; A61K 31/454; Y02A 50/30; A61P 31/12; C07D 239/96; C07D 401/06; C07D 409/06
See application file for complete search history.

(56) References Cited

U.S. PATENT DOCUMENTS 11,618,746 B2 4/2023 Cao et al.
11,801,234 B2 10/2023 Mallalieu et al.
11,866,446 B2 1/2024 Ahn et al.
2015/0297598 A1 10/2015 Friedman et al.
2018/0140587 A1 5/2018 Miao et al.

FOREIGN PATENT DOCUMENTS

WO WO 2009/003999 A2 1/2009
WO WO 2009/023655 A1 2/2009
WO WO 2018/213364 A1 11/2018
WO WO 2020/131807 A1 6/2020
WO WO 2021/154997 A1 8/2021
WO WO 2021/158666 A1 8/2021
WO WO 2021/178768 A1 9/2021
WO WO 2021/224927 A1 9/2021
WO WO 2021/252849 A1 12/2021
WO WO 2021/252859 A1 12/2021
WO WO 2021/252863 A1 12/2021
WO WO 2022/047031 A1 3/2022
WO WO 2023/028237 A1 3/2023
WO WO 2023/101981 A1 6/2023
WO WO 2023/154309 A1 8/2023
WO WO 2023/154310 A1 8/2023
WO WO 2023/154314 A1 8/2023
WO WO 2023/154344 A1 8/2023

OTHER PUBLICATIONS

Clark et al. Identification and development of the 1,4-benzodiazepin-2-one and quinazoline-2,4-dione scaffolds as submicromolar inhibitors of HAT (Bioorg. Med. Chem. 20, 6019-6033). (Year: 2012).*
Akhtar N., et al., "Structure-based pharmacophore models to probe anticancer activity of inhibitors of protein kinase B-beta," Chem Biol Drug Des., 2019, 93, 325-336.
Barakat Ses, et al. (1999) "Synthesis and biological screening of new 2,4-(1H,3H)quinazolinediones including 5-mercaptoxadiazole and 5-mercaptotriazole moieties," Azhar J. Pharm. Sci., vol. 23, pp. 36-45.
Hu C et al., "Human Apolipoprotein L1 (ApoL1) in Cancer and Chronic Kidney Disease (Review Paper)," FEBS Lett., 2012, 586(7), 947-955.
STN Registry RN 724422-01-9, Entered STN: Aug. 9, 2004.
STN Registry RN 838817-46-2, Entered STN: Feb. 27, 2005.
STN Registry RN 1185656-92-1, Entered STN: Sep. 18, 2009.
Aghajan M et al., "Antisense oligonucleotide treatment ameliorates IFN-gamma-induced proteinuria in APOL 1-transgenic mice", JCI insight, vol. 4, No. 12, 2019.
Botros, S., (1979), "Synthesis of some quinazoline compounds related to β-adrenergic blocking agents." *Pharmazie*, 34(11) pp. 746-747.
CAS Registry No. 341519-64-0. CA Index Name: benzoic acid, 4-[1,4-dihydro-6-nitro-2,4-dioxo-1-[2-(2-pyridinyl)ethyl]-3(2H)-quinazolinyl]-. Entered STN: Jun. 15, 2001.
CAS Registry No. 958579-04-9. CA Index Name: 2,4(1H,3H)-quinazolinedione, 3-(4-methylphenyl)-1-(3-pyridinylmethyl)-. Entered STN: Dec. 18, 2007.
CAS Registry No. 958564-62-0. CA Index Name: benzamide, N-cyclopentyl-4-[[1,4-dihydro-2,4-dioxo-1-(3-pyridinylmethyl)-3(2H)-quinazolinyl]methyl]-. Entered STN: Dec. 18, 2007.

(Continued)

*Primary Examiner* — Kamal A Saeed
*Assistant Examiner* — Meghan C Heasley
(74) *Attorney, Agent, or Firm* — Finnegan, Henderson, Farabow, Garrett & Dunner, LLP

(57) ABSTRACT

The invention in some embodiments thereof, relates to the field of compositions and/or pharmaceutical compositions comprising one or more biologically active compound, and is directed to methods of using same such as for treating an ApoL1 related disease or a disorder in a subject.

7 Claims, 4 Drawing Sheets

(56) References Cited

OTHER PUBLICATIONS

CAS Registry No. 899900-71-1. CA Index Name: 2,4(1H,3H)-quinazolinedione, 3-(4-ethylphenyl)-1-(3-pyridinylmethyl)-. Entered STN: Aug. 9, 2006.
Chun, J, et al. (2019) "Recruitment of APOL 1 kidney disease risk variants to lipid droplets attenuates cell toxicity", Proceedings of the National Academy of Sciences, 116(9), pp. 3712-3721.
Clark, RL, et al. (2012), "Identification and development of the 1,4-benzodiazepin-2-one and quinazoline-2,4-dione scaffolds as submicromolar inhibitors of HAT." *Bioorg. Med. Chem.* Oct. 15, 2012; 20(20): 6019-6033.
Glowacka, IE, et al. (2017) "Design, synthesis, and the biological evaluation of a new series of acyclic 1,2,3-triazole nucleosides." *Arch. Pharm.*, Sep. 2017; 350(9).
Huang, J, et al. (2018) "Glucocorticoids in the treatment of patients with primary focal segmental glomerulosclerosis and moderate proteinuria", Clinical and Experimental Nephrology, Japanese Society of Nephrology, 22(6), pp. 1315-1323.
International Search Report and Written Opinion for International Application No. PCT/IL2021/050521, mailed Jul. 11, 2021 (13 pages).
Nichols, B, et al. (2015) "Innate immunity pathways regulate the nephropathy gene Apolipoprotein LI." *Kidney international*, Feb. 1, 2015; 87(2): pp. 332-342.
Uckun, FM, et al. (1999) "In vivo toxicity and pharmacokinetic features of the janus kinase 3 inhibitor WHI-PI 31 [ 4-( 4'hydroxyphenyl)-amino-6, 7-dimethoxyquinazoline]" Clinical Cancer Research, Oct. 1, 1999: 5(10) p. 2954-2962.
Vertex Announces Positive Results From Phase 2 Study of VX-147 in APOL1-Mediated Focal Segmental Glomerulosclerosis, Vertex (Dec. 1, 2021), https://news.vrtx.com/press-release/vertex-announces-positive-results-phase-2-study-vx-147-apol1-mediated-focal-segmental (6 pages).
Yu, CW, et al. (2018) "Quinazolin-2,4-dione-based hydroxamic acids as selective histone deacetylase-6 inhibitors for treatment of non-small cell lung cancer." *J. Med. Chem*, Dec. 10, 2018; 62(2), pp. 857-874.

* cited by examiner

COMPOSITION FOR USE IN THE TREATMENT OF ApoL1-ASSOCIATED DISEASE

CROSS REFERENCE TO RELATED APPLICATIONS

This application claims the benefit of priority under 35 USC § 119(e) of U.S. Provisional Patent Application No. 63/021,222, filed May 7, 2020, entitled "COMPOSITION FOR USE IN THE TREATMENT OF APOL1-ASSOCIATED DISEASE" the contents of which are incorporated herein by reference in their entirety.

FIELD OF THE INVENTION

The invention relates generally to the field of compositions comprising inter alia one or more quinazolinedione derivatives and is directed to methods of using the same such as for treating a disease or disorder.

BACKGROUND

Apolipoprotein L1 (ApoL1) is a minor apoprotein component of High-density lipoprotein (HDL) which is synthesized in the liver and also in many other tissues, including pancreas, kidney, and brain. It is well known, that ApoL1 plays a role in innate immunity by protecting against Trypanosoma parasite infection in humans. Recently, it has been reported, that high frequency mutated variants of ApoL1 designated G1 and G2 (in contrast to the ancestral version designated as G0), are highly associated with kidney disease in humans with African ancestry. Many African Americans also have a high prevalence of ApoL1 risk alleles as well as ApoL1 associated kidney diseases. Since the discovery of the potential risk of G1 and G2 ApoL1 mutants, researchers have been trying to elucidate the cellular mechanisms of ApoL1 toxicity, so as to develop potential drug candidates for treating or preventing ApoL1 associated kidney disease.

SUMMARY

The following embodiments and aspects thereof are described and illustrated in conjunction with systems, tools and methods which are meant to be exemplary and illustrative, not limiting in scope.

In one aspect of the invention, there is a compound comprising one or more of the following compounds:

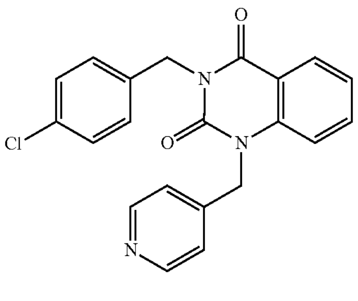

-continued

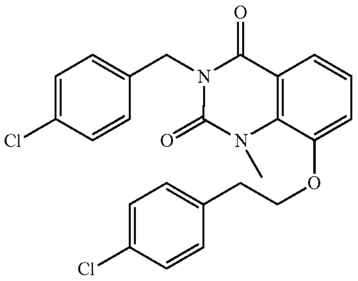

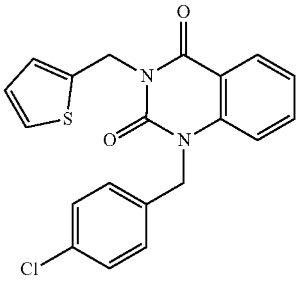

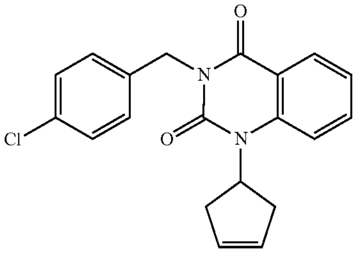

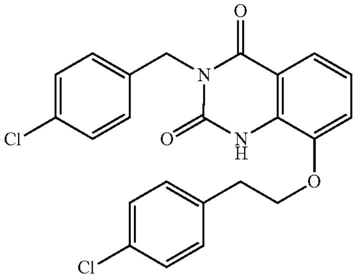

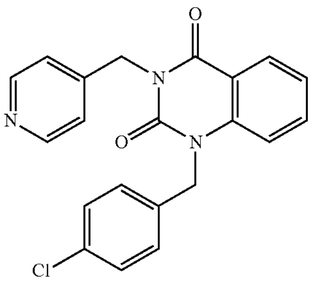

-continued

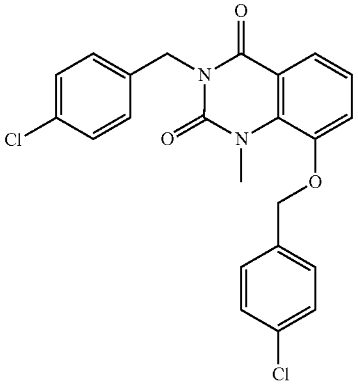

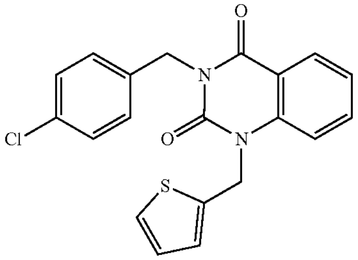

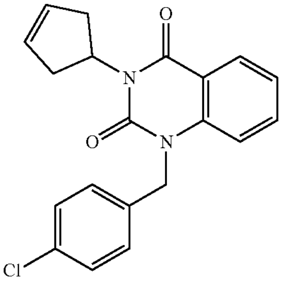

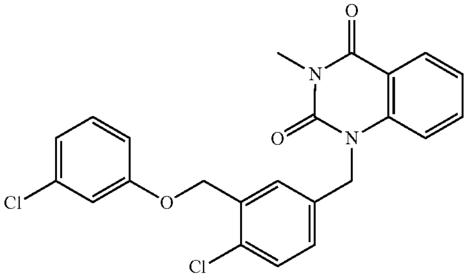

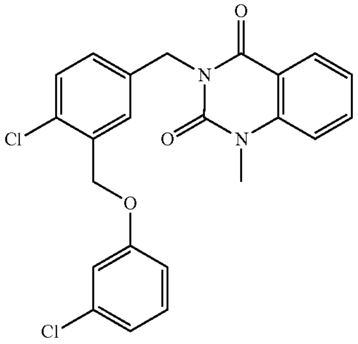

or a salt thereof.

In another aspect of the invention, there is a pharmaceutical composition, comprising (i) the compound of the invention, a pharmaceutically acceptable salt thereof or both, and (ii) a pharmaceutically acceptable carrier.

In another aspect of the invention, there is a pharmaceutical composition, comprising a compound represented by Formula 1:

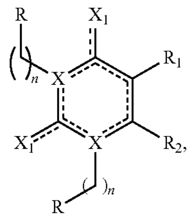

or by Formula 1A:

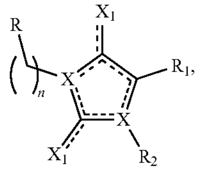

wherein each R, R1 and R2 independently comprises an alkyl, a cycloalkyl, a heterocyclyl, an aryl, a heteroaryl, hydrogen, a C1-C10 branched alkyl, a haloalkyl, a mercaptoalkyl, a heteroatom, a hydroxyalkyl, an aminoalkyl, a nitroalkyl, an alkylsulfate, a C1-C10 alkyl, a substituted C1-C10 alkyl or is absent; or R1 and R2 are interconnected so as to form a cyclic ring; each X1 independently comprises methylene, a heteroatom, —OR, —NRR, —SR, cyano, an alkyl, a carboxyl derivative, nitro, sulfonate, sulfonyl, or hydrogen; each X independently comprises methylene, a heteroatom or is absent; ------ represents a single or a double bond; and each n is from 0 to 10, or a pharmaceutically acceptable salt of the compound; and a pharmaceutically acceptable carrier for use in the inhibition or reduction of ApoL1 associated cell toxicity.

In one embodiment, the compound is represented by Formula 1C:

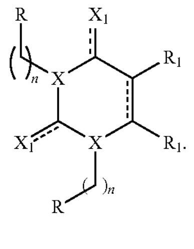

In one embodiment, the compound comprises

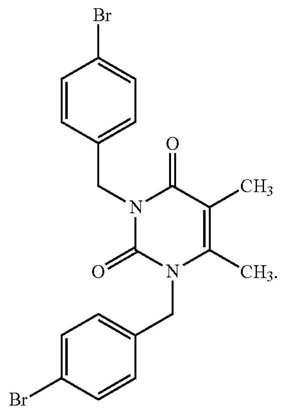 [SMILES: Cc1c(C)n(Cc2ccc(Br)cc2)c(=O)n(Cc2ccc(Br)cc2)c1=O]

In one embodiment, the compound is represented by Formula 2:

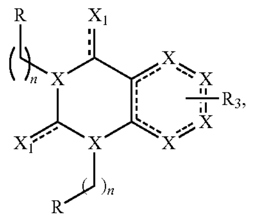

wherein R3 represents a substituent independently comprising at least one of a C1-C10 alkyl, a C1-C10 branched alkyl, a substituted C1-C10 alkyl, halo, a hydroxy, an amino, mercapto, cyano, a carboxylic acid derivative, nitro, guanidine, an aryl, a heteroaryl, benzyl, an alkaryl, a cycloalkyl, a heterocyclyl, a heteroatom, hydrogen or is absent.

In one embodiment, the compound is represented by Formula 3:

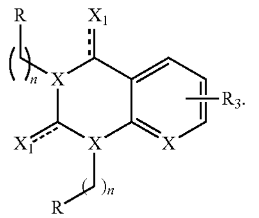

In one embodiment, the compound is represented by Formula 4:

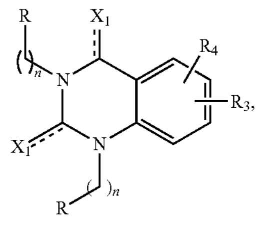

wherein: n is between 0 and 5; each R3 represents a substituent independently comprising

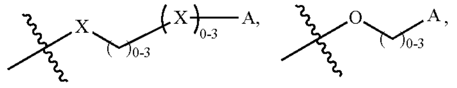

or is absent, wherein A represents an optionally substituted aliphatic (C3-C20) ring, an optionally substituted aromatic (C5-C20) ring or is absent; and each R4 represents a substituent independently comprising hydrogen, an C1-C10 alkyl, a C1-C10 branched alkyl, a substituted C1-C10 alkyl, halo, nitro, hydroxy, mercapto, amino, cyano, and a carboxyl derivative, or any combination thereof.

In one embodiment, each R3 is independently selected from the group comprising:

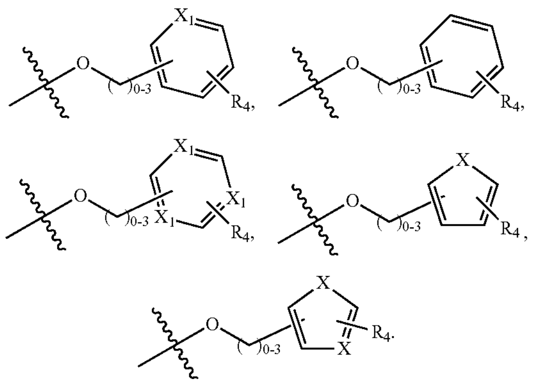

In one embodiment, the compound is represented by any of the Formulae 7A-C:

Formula 7A

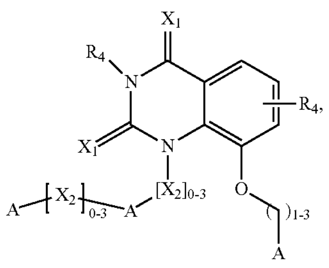

Formula 7B

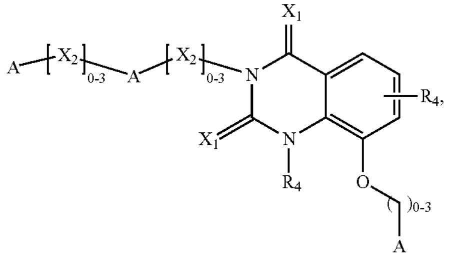

-continued

Formula 7C

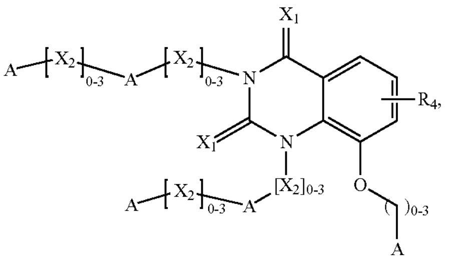

wherein each X2 is independently selected from the group comprising methylene, a heteroatom, alkyl, halo, an alkoxy, an a hydroxy, an amino, a thioalkoxy, a mercapto, a cyano, a carboxylic acid derivative a nitro, a guanidine, a heteroatom, aryl, heteroaryl, benzyl, an alkylaryl, a cycloalkyl, a heterocyclyl, a bond and hydrogen or any combination thereof.

In one embodiment, each X1 independently comprises a heteroatom, and each X is independently selected from the group comprising —N—, —NH, —O—, and —S—.

In one embodiment, the substituted C1-C10 alkyl comprises a substituent selected from the group comprising halo, mercapto, hydroxy, amino, a carboxyl derivative, cyano, nitro, sulfonate, and sulfonyl or any combination thereof.

In one embodiment, the compound comprises any of:

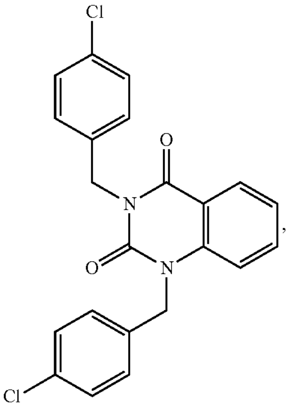

,

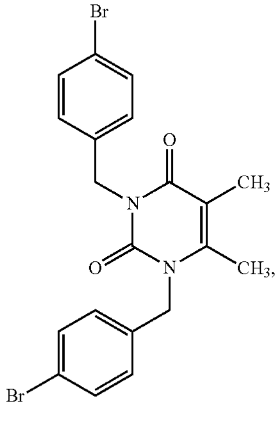

,

-continued

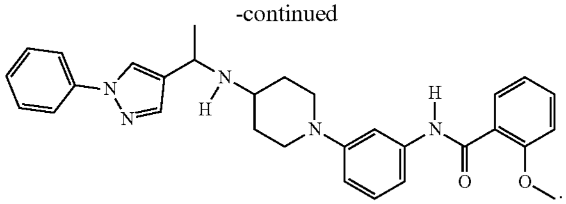

.

In one embodiment, the inhibition or reduction of ApoL1 associated cell toxicity comprises prevention or treatment of ApoL1 associated kidney disease.

In one embodiment, the ApoL1 associated cell toxicity is an ApoL1 mutant associated cell toxicity.

In another aspect of the invention, there is a method for inhibiting or reducing ApoL1 associated cell toxicity in a subject in need thereof, comprising administering a pharmaceutical composition comprising a compound represented by Formula 1:

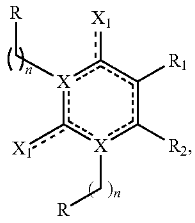

, or by Formula 1A:

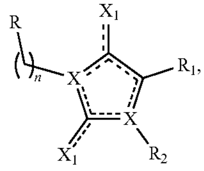

, wherein:

each R, R1 and R2 independently comprises an alkyl, a cycloalkyl, a heterocyclyl, an aryl, a heteroaryl, hydrogen, a C1-C10 branched alkyl, a haloalkyl, a mercaptoalkyl, a heteroatom, a hydroxyalkyl, an aminoalkyl, a nitroalkyl, an alkylsulfate, a C1-C10 alkyl, a substituted C1-C10 alkyl or is absent; or R1 and R2 are interconnected so as to form a cyclic ring; each X1 independently comprises methylene, a heteroatom, —OR, —NRR, —SR, cyano, an alkyl, a carboxyl derivative, nitro, sulfonate, sulfonyl, or hydrogen; each X independently comprises methylene, a heteroatom or is absent, ------ represents a single or a double bond; and each n is from 0 to 10, or a pharmaceutically acceptable salt of said compound; and a pharmaceutically acceptable carrier, thereby inhibiting or reducing ApoL1 associated cell toxicity in said subject.

In one embodiment, inhibiting or reducing ApoL1 associated cell toxicity comprises preventing or treating ApoL1 associated kidney disease.

In one embodiment, the ApoL1 associated cell toxicity is an ApoL1 mutant associated cell toxicity.

In addition to the exemplary aspects and embodiments described above, further aspects and embodiments will become apparent by reference to the figures and by study of the following detailed description.

BRIEF DESCRIPTION OF THE DRAWINGS

FIG. 1A: Incubation with various concentrations (0, 0.08, 0.156, 0.3, 0.6, 1.25, 2.5, 5 and 10 μM) of compound 1. FIG. 1B: Incubation with various concentrations (0, 0.08, 0.156, 0.3, 0.6, 1.25, 2.5, 5 and 10 μM) of compound 3. FIG. 1C: Incubation with various concentrations (0, 0.156, 0.313, 0.625, 1.25, 2.5, 5 and 10 μM) of compound 7.

DETAILED DESCRIPTION

Figure 1A:
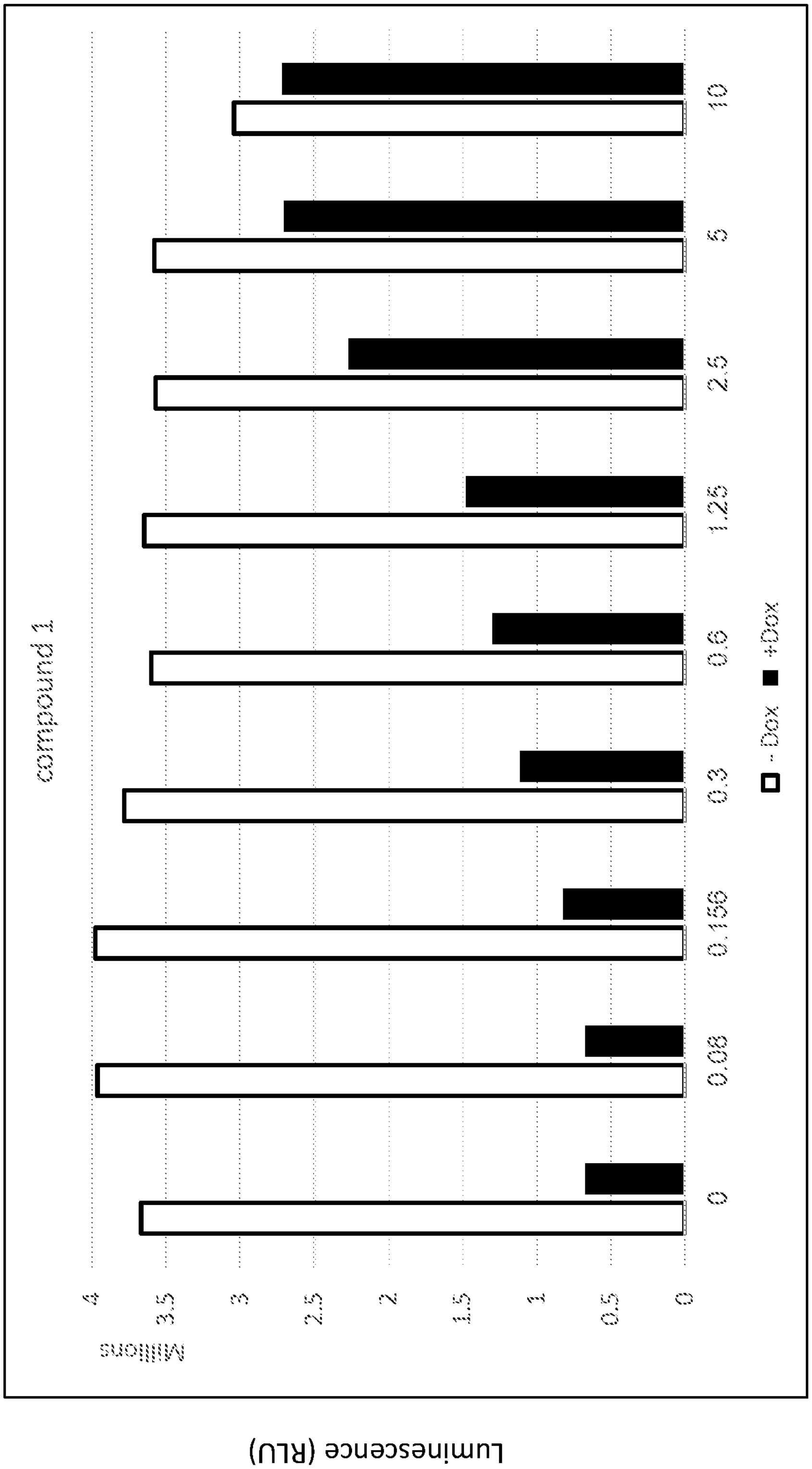
FIGS. 1A-C are bar graphs representing viability of T-REx-293 cells after 16 hours incubation with exemplary compound of the invention at various concentrations, versus a non-treated control. Black bars represent cell count of cells expressing ApoL1 G1 (activated by Doxycycline). White bars represent cell count of cells expressing a wild-type ApoL1.

In one aspect of the invention disclosed herein, there is provided a compound, a salt or a derivative thereof, wherein the compound is represented by Formula 1.2:

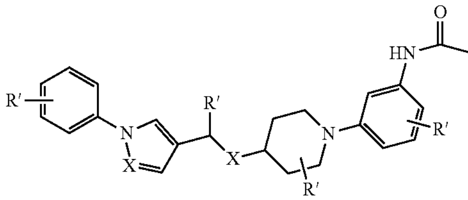

wherein each X independently comprises methylene, a heteroatom or is absent; each R' independently comprises $(C_0-C_6)$alkyl-aryl, $(C_0-C_6)$alkyl-heteroaryl, $(C_0-C_6)$alkyl-$(C_3-C_8)$ cycloalkyl, optionally substituted $C_3-C_5$ heterocyclyl, halogen, —$NO_2$, —CN, —OH, —$CONH_2$, —$CONR''_2$, —CNNR"2, —$CSNR''_2$, —CONH—OH, —CONH—$NH_2$, —NHCOR", —NHCSR", —NHCNR", —NC(═O)OR", —NC(═O)NR", —NC(═S)OR", —NC(═S)NR", —$SO_2R''$, —SOR", —SR", —$SO_2OR''$, —$SO_2N(R)_2$, —$NHNR_2$, —NNR, $C_1-C_{10}$ haloalkyl, optionally substituted $C_1-C_{10}$ alkyl, —$NH_2$, —NH($C_1-C_{10}$ alkyl), —N($C_1-C_{10}$ alkyl$)_2$, $C_1-C_{10}$ alkoxy, $C_1-C_{10}$ haloalkoxy, hydroxy($C_1-C_{10}$ alkyl), hydroxy($C_1-C_{10}$ alkoxy), alkoxy ($C_1-C_{10}$ alkyl), alkoxy ($C_1-C_{10}$ alkoxy), $C_1-C_{10}$ alkyl-NR" 2, $C_1-C_{10}$ alkyl-SR, —CONH($C_1-C_{10}$ alkyl), —CON($C_1-C_{10}$ alkyl$)_2$, —$CO_2H$, —$CO_2R''$, —OCOR", —OCOR", —OC(═O)OR", —OC(═O)NR", —OC(═S)OR", —OC(═S)NR", including any combination thereof; and wherein R" is selected from optionally substituted $C_1-C_{10}$ alkyl, and hydrogen.

In some embodiments, the heteroatom is independently selected from the group consisting of O, N, NH, and S. In some embodiments, the heteroatom is N.

In some embodiments, the compound of the invention is represented by Formula 1.2A:

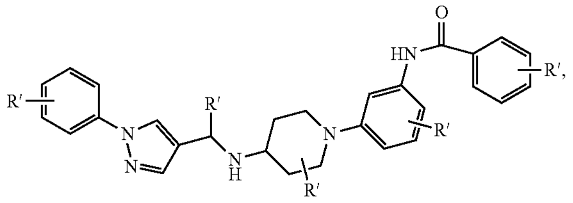

or by Formula 1.3:

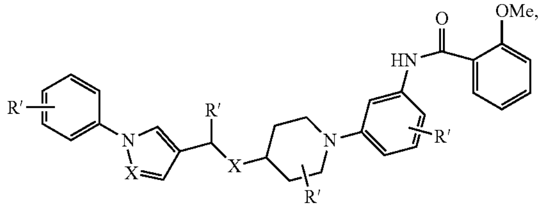

wherein X and R' are as described hereinabove.

In some embodiments, the compound of the invention is or comprises

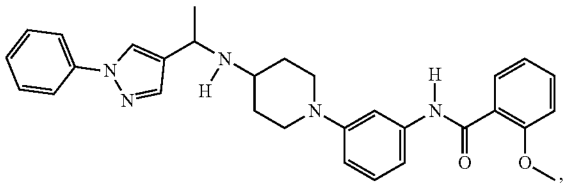 [SMILES: COc1ccccc1C(=O)Nc1cccc(N2CCC(NC(C)c3cnn(-c4ccccc4)c3)CC2)c1]

(also referred to herein as compound 7), wherein the compound optionally comprises any salt or any derivative thereof.

In another aspect of the invention, there is provided a compound represented by Formula 1:

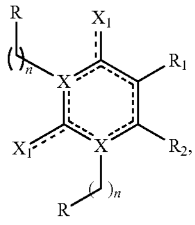

wherein each R, R1 and R2 independently comprises an alkyl, a cycloalkyl, a heterocyclyl, an aryl, a heteroaryl, hydrogen, a C1-C10 branched alkyl, a haloalkyl, a mercaptoalkyl, a heteroatom, a hydroxyalkyl, an aminoalkyl, a nitroalkyl, an alkylsulfate, optionally substituted C1-C10 alkyl, or is absent; or R1 and R2 are interconnected so as to form a cyclic ring; each X1 independently comprises methylene, a heteroatom, —OR", —NR"R", —SR", cyano, an alkyl, a carboxyl derivative, nitro, sulfonate, sulfonyl, or hydrogen; R" is as described herein, each X independently comprises CH, CH2, a heteroatom or is absent; ----- represents a single or a double bond; and each n is from 0 to 10.

In some embodiments, each n independently represents an integer ranging from 0 to 10, from 0 to 1, from 1 to 2, from 2 to 4, from 4 to 6, from 6 to 10, including any range between.

In some embodiments, the heteroatom is independently selected from the group consisting of O, N, NH, and S. In some embodiments, the heteroatom is N.

In some embodiments, each of R1 and R2 independently comprises R' or H, wherein R' is as described herein. In some embodiments, each of R1 and R2 independently comprises optionally substituted C1-C10 alkyl, halo, sulfonate, sulfonyl, nitro, hydroxy, mercapto, amino, cyano, a carboxyl derivative, alkylhydroxy, aminoalkyl, mercaptoalkyl, $CONH_2$, —CONR"2, —CNNR"2, —CSNR"$_2$, —CONH—OH, —CONH—$NH_2$, —NHCOR", —NHCSR", —NHCNR", —NC(═O)OR", —NC(═O)NR", —NC(═S)OR", —NC(═S)NR", —$CO_2$H, —$CO_2$R", —OCOR", —OCOR", —OC(═O)OR", —OC(═O)NR", —OC(═S)OR", —OC(═S)NR", or H, including any combination or any salt thereof.

In some embodiments, each of R1 and R2 independently comprises H or C1-C10 alkyl optionally comprising one or more substituent selected from the group consisting of halo, sulfonate, sulfonyl, nitro, hydroxy, mercapto, amino, cyano, a carboxyl derivative, alkylhydroxy, aminoalkyl, mercaptoalkyl, or any combination thereof. In some embodiments, each of R1 and R2 independently comprises H or C1-C10 alkyl optionally substituted by one or more R'. In some embodiments, each R1 and R2 independently comprises an alkyl, hydrogen, a cycloalkyl, a heterocyclyl, an aryl, a heteroaryl, or is absent.

In some embodiments, the cyclic ring is an aliphatic cycloalkyl, an aliphatic heterocyclyl, an aromatic ring, a heteroaromatic ring or a combination thereof. In some embodiments, the cyclic ring is a fused ring. In some embodiments, the cyclic ring is a bicyclic ring. In some embodiments, the cyclic comprises one or more substituents, wherein the substituent is as described herein.

In some embodiments, the compound of the invention is represented by any one of:

Formula 1A

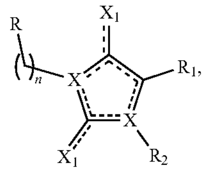

Formula 1B

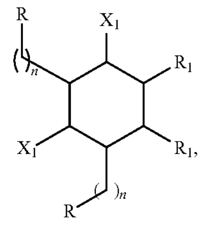

Formula 1C

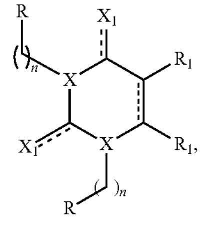

wherein X, X1, R, R1, R2 and n are as described hereinabove.

In some embodiments, the compound of the invention is represented by Formula 1C, wherein each R independently comprises a substituted or a non-substituted cycloalkyl, a substituted or a non-substituted heterocyclyl, a substituted or a non-substituted aryl, a substituted or non-substituted heteroaryl; X is N or CH; and wherein X1 is 0 or OH. In some embodiments, substituted is by one or more (e.g. 1, 2, 3, 4) R'.

In some embodiments, the compound of the invention is represented by Formula1D:

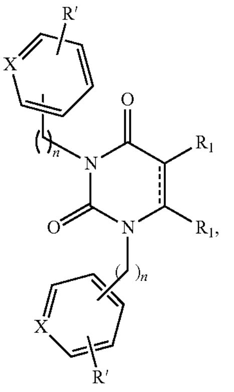

wherein each R1 independently comprises a substituted or non-substituted cycloalkyl, a substituted or non-substituted heterocyclyl, a substituted or non-substituted aryl, a substituted or non-substituted heteroaryl, hydrogen, a haloalkyl, a mercaptoalkyl, a heteroatom, a hydroxyalkyl, an aminoalkyl, a nitroalkyl, an alkylsulfate, a substituted or non-substituted C1-C10 alkyl, or any combination thereof; and wherein R1, R' n, and X are as described herein. In some embodiments, the compound of the invention is represented by Formula1D, wherein each R1 is a substituted or non-substituted C1-C10 alkyl, wherein n is independently 0 to 5 (e.g. is selected from 0, 1, 2, and 3); and wherein each R' is a halogen or is absent.

In some embodiments, the compound of the invention is or comprises:

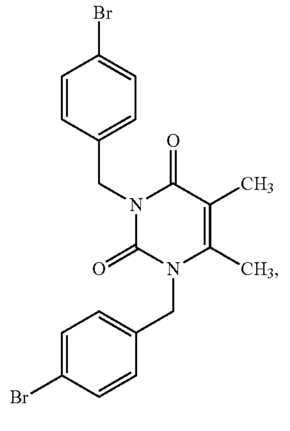

also referred to herein as compound 1, optionally comprising any salt or any derivative thereof.

In some embodiments, the compound of the invention is represented by Formula 2:

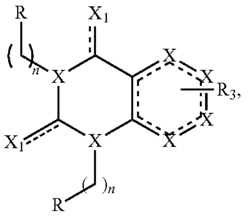

wherein R3 represents a substituent independently comprising an alkyl, halo, an alkoxy, an a hydroxy, an amino, a thioalkoxy, a mercapto, a cyano, a carboxylic acid derivative a nitro, a guanidine, a heteroatom, aryl, heteroaryl, benzyl, an alkaryl, a cycloalkyl, a heterocyclyl, hydrogen or is absent; and wherein X, X1, R, and n are as described hereinabove. In some embodiments, R3 represents a substituent independently comprising at least one of a C1-C10 alkyl, a C1-C10 branched alkyl, a substituted C1-C10 alkyl, halo, a hydroxy, an amino, mercapto, cyano, a carboxylic acid derivative, nitro, guanidine, an aryl, a heteroaryl, benzyl, an alkaryl, a cycloalkyl, a heterocyclyl, a heteroatom, hydrogen or is absent.

In some embodiments, the compound of the invention is represented by any one of:

Formula 2A:

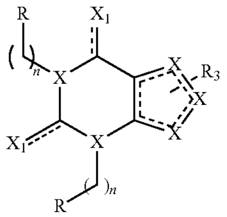

Formula 3:

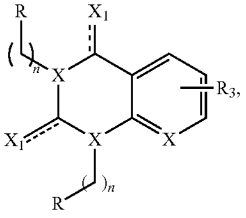

wherein X, X1, R, R1, R2, R3 and n are as described hereinabove.

In some embodiments, the compound of the invention is selected from Formulae 3A-D:

Formula 3A

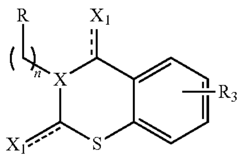

Formula 3B

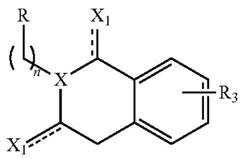

-continued

Formula 3C

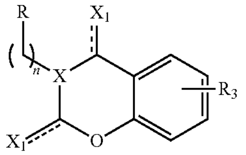

Formula 3D

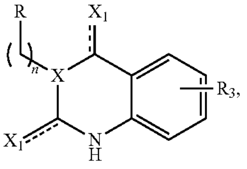

wherein X, X1, R, R3 and n are as described hereinabove.

In some embodiments, the compound of the invention is represented by any one of:

Formula 3E:

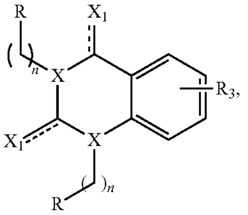

Formula 3F:

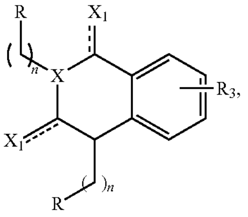

Formula 3G:

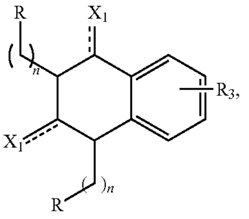

wherein X, X1, R, R3 and n are as described hereinabove.

In some embodiments, R3 is hydrogen. In some embodiments, each R3 independently comprises any of:

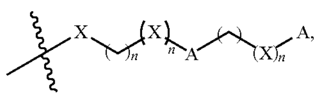

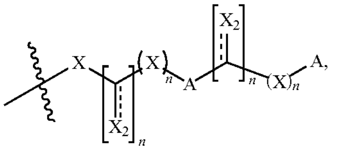

-continued

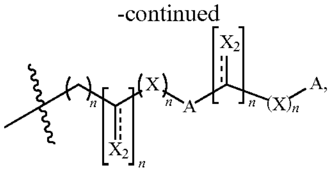

wherein a dashed line represents a single bond or a double bond; wherein each X2 independently comprises at least one of: methylene, a heteroatom, alkyl, halo, an alkoxy, an a hydroxy, an amino, a thioalkoxy, a mercapto, a cyano, a carboxylic acid derivative a nitro, a guanidine, a heteroatom, aryl, heteroaryl, benzyl, an alkylaryl, a cycloalkyl, a heterocyclyl, a bond or hydrogen; wherein each A independently represents an optionally substituted aliphatic (C3-C20) ring, an optionally substituted aromatic (C5-C20) ring or is absent; and wherein X, and n are as described hereinabove.

In some embodiments, a dashed line represents a single bond and each X2 independently comprises at least one of: alkyl, halo, an alkoxy, a hydroxy, an amino, a thioalkoxy, a mercapto, a cyano, a carboxylic acid derivative a nitro, a guanidine, a heteroatom, aryl, heteroaryl, benzyl, an alkaryl, a cycloalkyl, a heterocyclyl, a bond and hydrogen.

In some embodiments, a dashed line represents a double bond and each X2 independently comprises at least one of: methylene, a heteroatom, a cycloalkyl, and a heterocyclyl. In some embodiments, a dashed line represents a double bond and each X2 independently comprises a heteroatom. In some embodiments, X2 represents a bond.

In some embodiments, R3 comprises hydrogen or

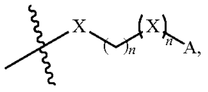

wherein X is a heteroatom or is absent; A represents an optionally substituted aliphatic (C3-C20) ring, or an optionally substituted aromatic (C5-C20) ring; and wherein n is between 0 and 5.

In some embodiments, A represents an optionally substituted aliphatic (C5-C7) ring, an optionally substituted heterocyclic aliphatic (C5-C7) ring, an optionally substituted aromatic (C5-C6) ring, or an optionally substituted heteroaromatic (C5-C6) ring. In some embodiments, A represents an optionally substituted bicyclic aliphatic (C6-C15) ring, an optionally substituted bicyclic aromatic (C6-C15) ring, an optionally substituted fused (C6-C15) ring. In some embodiments, A represents an optionally substituted aliphatic (C5-C7) ring, or an optionally substituted aromatic (C5-C6) ring.

In some embodiments, the compound of the invention is represented by Formula 4:

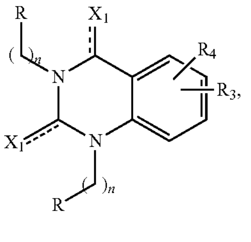

wherein X1, R and R3 are as described hereinabove, n is between 0 and 5 and R4 is as described hereinbelow.

In some embodiments, each X1 independently represents a heteroatom or methylene. In some embodiments, a dashed bond is a double bond.

In some embodiments, R3 is hydrogen or

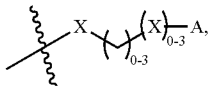

wherein X and R are as described hereinabove. In some embodiments, each X is independently selected from —NH, —O—, and —S— or is absent.

In some embodiments, R3 is hydrogen or

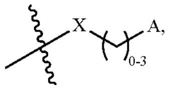

wherein X and A are as described hereinabove.

In some embodiments, R3 is hydrogen or

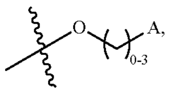

wherein R is as described hereinabove.

In some embodiments, R3 is hydrogen. In some embodiments, each R3 is independently selected from:

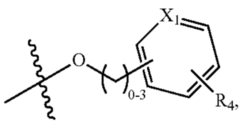

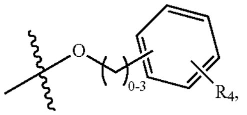

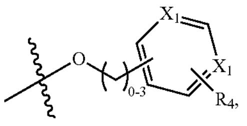

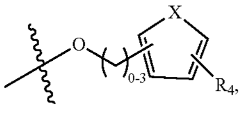

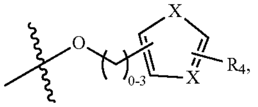

wherein R4 comprises any of hydrogen, an alkyl, a C1-C10 branched alkyl, a haloalkyl, a mercaptoalkyl, a heteroatom, a hydroxyalkyl, an aminoalkyl, a nitroalkyl, an alkylsulfate, a C1-C10 alkyl optionally comprising a substituent selected from the group consisting of halo, nitro, hydroxy, mercapto, amino, cyano, a carboxyl derivative, alkylhydroxy, aminoalkyl, mercaptoalkyl, or any combination thereof; and wherein X, and X1 are as described hereinabove. In some embodiments, R3 represents one or more substituents. In some embodiments, ach X1 is independently selected from N and CH. In some embodiments, each X is independently selected from the group comprising —N—, —NH, —O—, and —S—.

In some embodiments, the compound of the invention is represented by Formula 5:

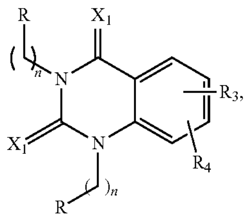

wherein X1 is selected from the group comprising O, S, and NH; and wherein R, R3 and n are as described hereinabove.

In some embodiments, the compound of the invention is represented by any one of:

Formula 6A:

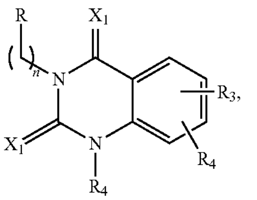

Formula 6B:

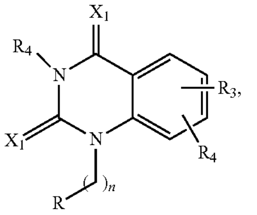

Formula 6C:

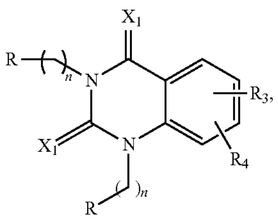

wherein R, R3, n and X1 are as described herein; and wherein R4 is as described hereinabove. In some embodiments, R4 is hydrogen or a C1-C10 alkyl. In some embodiments, R4 is hydrogen.

In some embodiments, the compound of the invention is represented by Formula 4.1:

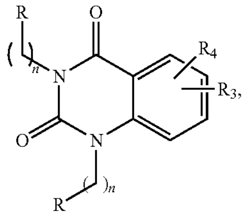

wherein n is between 0 and 5; each R3 represents a substituent independently comprising

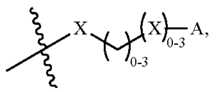

or

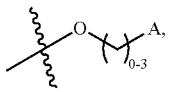

or wherein R3 is absent; wherein A represents an optionally substituted aliphatic (C3-C20) ring, an optionally substituted aromatic (C5-C20) ring or H; and R4 represents a substituent independently comprising hydrogen, an C1-C10 alkyl, a C1-C10 branched alkyl, a substituted C1-C10 alkyl, halo, nitro, hydroxy, mercapto, amino, cyano, and a carboxyl derivative, or any combination thereof. In some embodiments, each X is independently selected from the group comprising —N—, —NH, —O—, and —S—.

In some embodiments, the compound of the invention is or comprises:

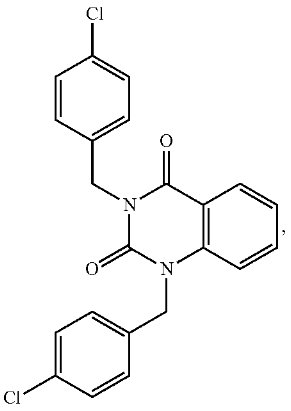 [SMILES: O=c1c2ccccc2n(Cc2ccc(Cl)cc2)c(=O)n1Cc1ccc(Cl)cc1]

also referred to herein as compound 3, and optionally comprising any salt or any derivative thereof.

In some embodiments, the compound of the invention is represented by any one of:

Formula 7A

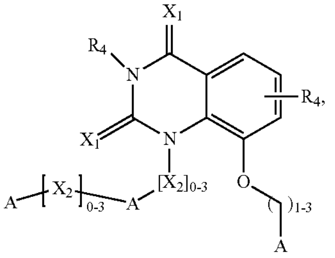

Formula 7B

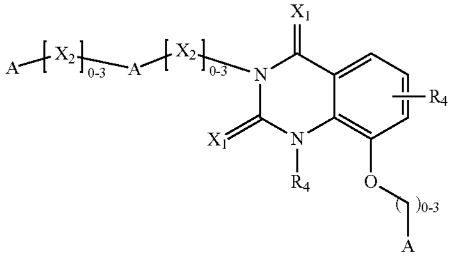

or by Formula 7C:

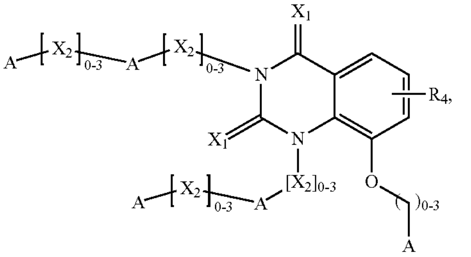

wherein R4, X2, A, X1 and n are as described hereinabove, and wherein ------ represents a single or a double bond. In some embodiments, the compound of the invention is represented by any one of Formulae 7A-C, wherein each X2 is independently selected from the group comprising methylene, a heteroatom, alkyl, halo, an alkoxy, an a hydroxy, an amino, a thioalkoxy, a mercapto, a cyano, a carboxylic acid derivative a nitro, a guanidine, a heteroatom, aryl, heteroaryl, benzyl, an alkylaryl, a cycloalkyl, a heterocyclyl, a bond and hydrogen or any combination thereof; and wherein each X1 is 0. In some embodiments, R4 is hydrogen or a C1-C10 alkyl.

In some embodiments, the compound of the invention is represented by Formula 8A:

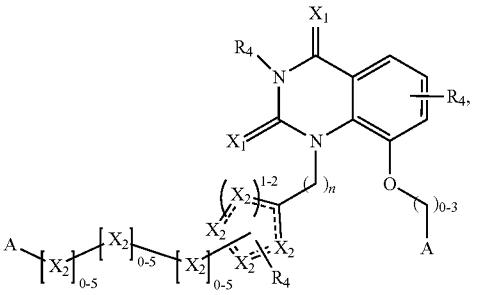

or by Formula 8B:

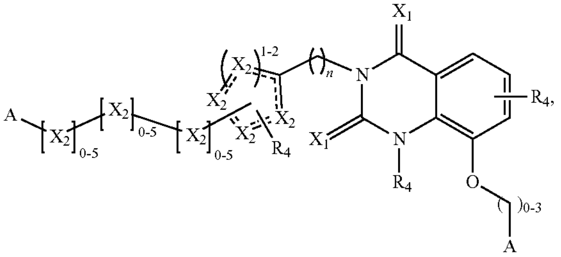

or by Formula 8C:

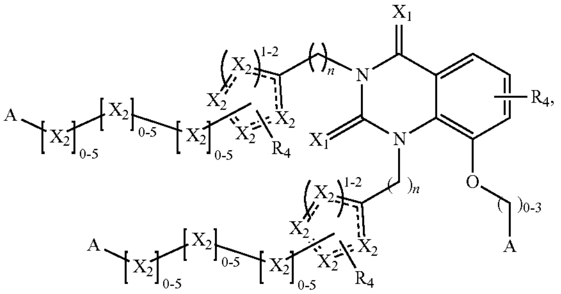

wherein R4, X2, A, X1 and n are as described hereinabove, and wherein ------ represents a single or a double bond.

In some embodiments, X1 is oxygen. In some embodiments, each X2 is independently selected from methylene, —N—, —NH, —O—, and —S—.

In some embodiments, the compound of the invention is represented by any of Formulae 9A-F:

Formula 9A

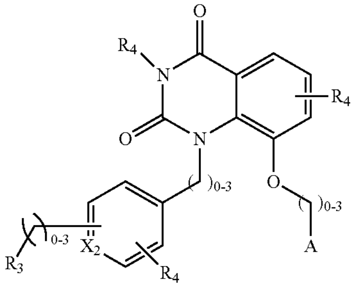

Formula 9B

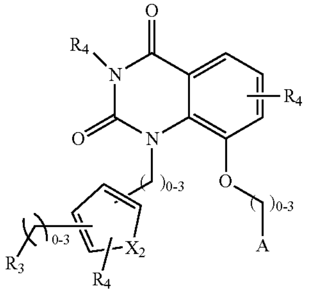

-continued

Formula 9C

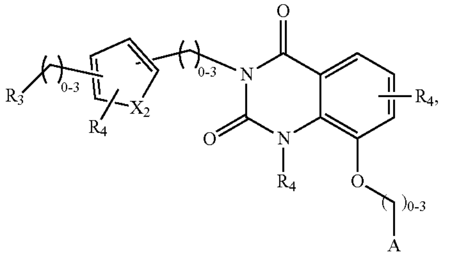

Formula 9D

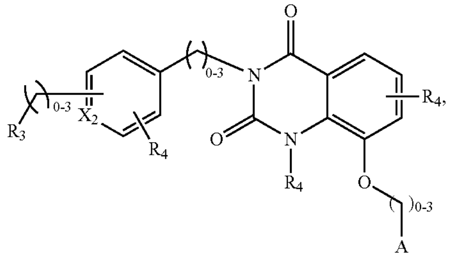

Formula 9E

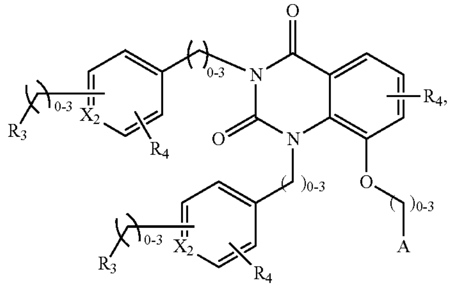

Formula 9F

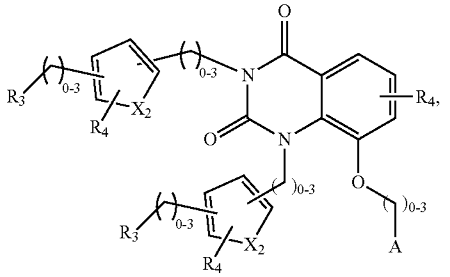

wherein R4, R3, X2, and A, are as described hereinabove.

In some embodiments, the compound of the invention is represented by Formula 9G:

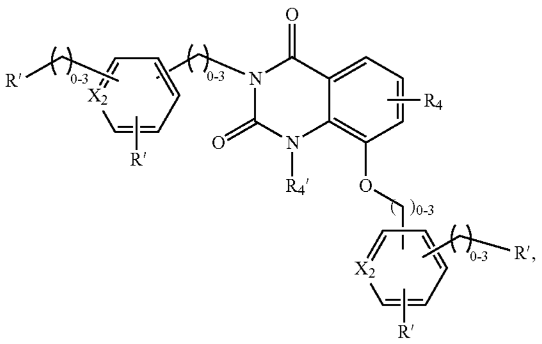

wherein R4, R', and X2, are as described hereinabove, and wherein R4' is C1-C10 alkyl or is absent. In some embodiments, the compound of the invention is represented by Formula 9G and X2 is methylene or N.

In some embodiments, the compound of the invention is represented by Formula 6D:

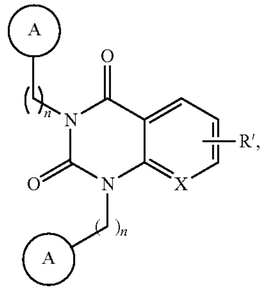

wherein R' and n are as described hereinabove; wherein X is CH or N; and wherein each A independently represents (C3-C20) cycloalkyl, (C3-C20) heterocyclyl (optionally comprising an unsaturated bond), aryl or heteroaryl, and wherein at least one A is (C3-C20) heterocyclyl or heteroaryl. In some embodiments, each A is optionally substituted by one or more R' comprising $(C_0-C_6)$alkyl-aryl, $(C_0-C_6)$alkyl-heteroaryl, $(C_0-C_6)$alkyl-$(C_3-C_8)$ cycloalkyl, optionally substituted $C_3-C_8$ heterocyclyl, halogen, —$NO_2$, —CN, —OH, —$CONH_2$, —CONR"2, —$CNNR''_2$, —$CSNR''_2$, —CONH—OH, —CONH—$NH_2$, —NHCOR", —NHCSR", —NHCNR", —NC(═O)OR", —NC(═O)NR", —NC(═S)OR", —NC(═S)NR", —$SO_2R''$, —SOR", —SR", —$SO_2OR''$, —$SO_2N(R)_2$, —$NHNR_2$, —NNR, $C_1-C_{10}$ haloalkyl, optionally substituted $C_1-C_{10}$ alkyl, —$NH_2$, —NH($C_1-C_{10}$ alkyl), alkyl)$_2$, $C_1-C_{10}$ alkoxy, haloalkoxy, hydroxy($C_1-C_{10}$ alkyl), hydroxy($C_1-C_{10}$ alkoxy), alkoxy($C_1-C_{10}$ alkyl), alkoxy($C_1-C_{10}$ alkoxy), alkyl-$NR''_2$, $C_1-C_{10}$ alkyl —SR, —CONH($C_1-C_{10}$ alkyl), —CON($C_1-C_{10}$ alkyl)$_2$, —$CO_2H$, —$CO_2R''$, —OCOR", —OCOR", —OC(═O)OR", —OC(═O)NR", —OC(═S)OR", or —OC(═S)NR", including any combination thereof.

In some embodiments, the compound of the invention is represented by Formula 6E:

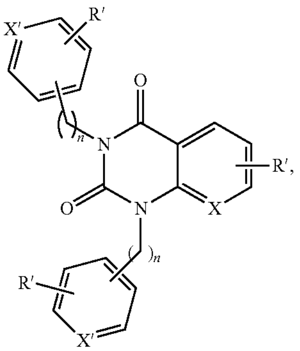

wherein X, n, and R' are as described herein, wherein X' is N or CH, and at least one X' is N. In some embodiments, both X' are N.

In some embodiments, the compound of the invention is any of:

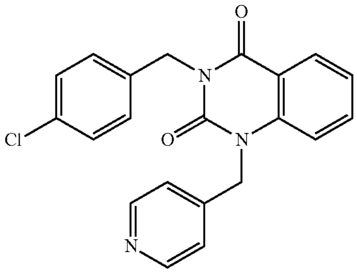
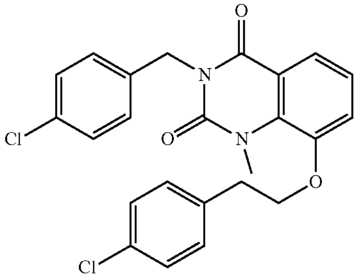
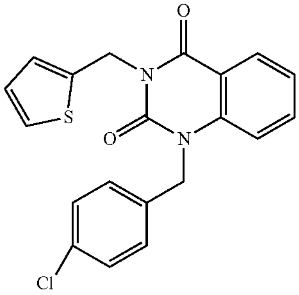
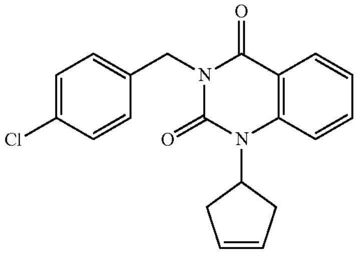
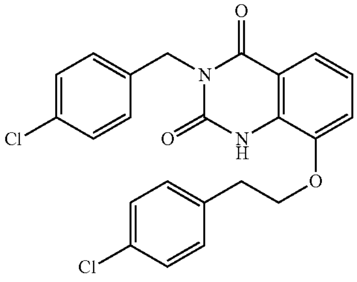
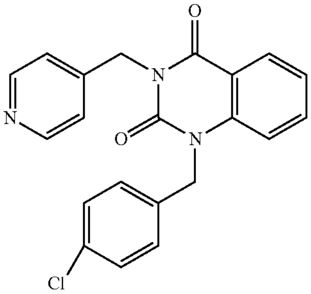
including any salt and/or any derivative thereof.
In some embodiments, the compound of the invention is any of:
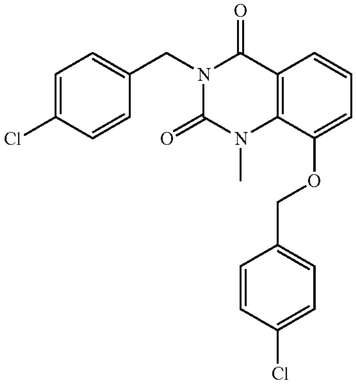
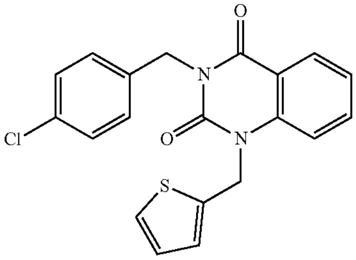
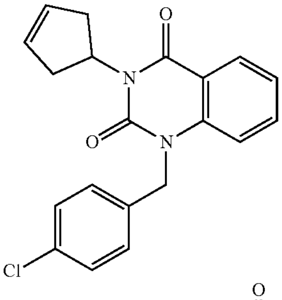
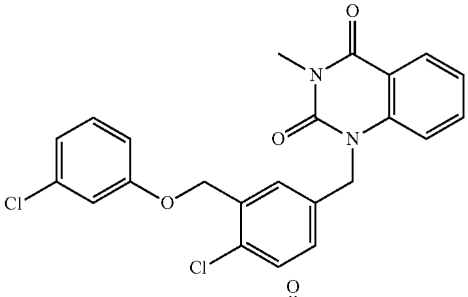
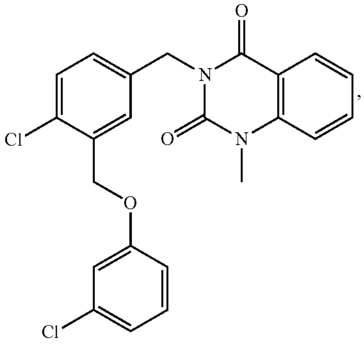
,
including any salt and/or any derivative thereof.
As used herein, the term "stereoisomer" refers to an enantiomer or to a diastereomer of the compound.

In some embodiments, the term "derivative" refers to a prodrug of the compound, such as ester; a tautomer of the compound, such as keto-enol tautomer, imine-enamine tautomer, amide-iminol tautomer, including any combination thereof. In some embodiments, the term "derivative" refers to a compound substituted by one or more (e.g. 2, 3, 4, or 5) substituents, optionally wherein any one of the substituents is independently R', wherein R' is as described herein.

In some embodiments, there is provided herein a composition comprising one or more compounds of the invention, including any salt (e.g. a pharmaceutically acceptable salt), any tautomer, and/or any stereoisomer thereof. In some embodiments, the compound as described hereinabove is the only active ingredient within the composition of the invention (e.g. pharmaceutical composition).

In some embodiments, the composition of the invention is a pharmaceutical composition comprising at least one compound of the invention and a pharmaceutically acceptable carrier. In some embodiments, the composition of the invention is a pharmaceutical composition comprising at least one compound of the invention as a first active ingredient and an additional active ingredient.

In some embodiments, the pharmaceutical composition is in a form of a combination or of a kit of parts. In some embodiments, the pharmaceutical composition of the invention is for use as a medicament.

Method of Treatment

In another aspect, there is provided a method for inhibiting or reducing ApoL1 associated cell toxicity in a subject in need thereof, the method comprising administering to the subject the pharmaceutical composition or the compound of the invention. In some embodiments, administering is by an oral administration, a systemic administration or a combination thereof.

In some embodiments, the method is for preventing or treating a disease or disorder associated with ApoL1. In some embodiments, the method is for preventing or treating a disease or disorder associated with expression of ApoL1 mutant allele within a subject. In some embodiments, the method is for preventing or treating a disease or disorder associated with overexpression of ApoL1 (mutant and/or wildtype) within a subject. In some embodiments, overexpression comprises enhanced intracellular concentration of ApoL1.

In some embodiments, ApoL1 associated cell toxicity comprises ApoL1 induced endo-lysosomal disturbance, ApoL1 induced mitochondrial dysfunction (such as by reducing mitochondrial respiration rate), ApoL1 induced increased potassium efflux, inflammasome activation, protein aggregation, protein-protein interaction, unfolded protein response, pyroptosis, necroptosis, ferroptosis, autophagy inhibition, or any combination thereof.

In some embodiments, ApoL1 is an ApoL1 mutant (such as ApoL1 G1 and/or ApoL1 G2). The sequence of ApoL1 G1/G2 mutant alleles is well-known in the art.

In some embodiments, the method of the invention comprises the steps of: determining whether an expression level of at least one ApoL1 gene is increased (e.g. by at least 10%, at least 50%, at least 100%, at least 200%, at least 300%, at least 1000%, including any range between) above a pre-determined threshold, in a sample obtained or derived from a subject; and administering to the subject determined as having increased expression level of at least one ApoL1 gene above a pre-determined threshold, a therapeutically effective amount of a compound of the invention, thereby treating a disease or disorder associated with ApoL1 in the subject. In some embodiments, the disease or disorder associated with ApoL1 is or comprises a disease or disorder associated with overexpression of ApoL1 gene within a subject. In some embodiments, the ApoL1 gene is a wildtype gene or a mutant gene (G1 and/or G2).

In some embodiments, the method of the invention comprises: determining whether a G1 mutation ($S_{342}$>G and/or $I_{384}$>M) or G2 mutation (e.g. 6 bp deletion N388del: Y389del), or both, are present in a ApoL1 gene of a cell of a subject (e.g. a kidney cell); and administering to the subject determined as having a cell comprising the G1 and/or G2 mutation in the ApoL1 gene, a therapeutically effective amount of a compound of the invention, thereby treating a disease or disorder associated with ApoL1 in the subject. In some embodiments, the disease or disorder associated with ApoL1 is or comprises a disease or disorder associated with expression of ApoL1 mutant allele (e.g. G1 and/or G2) within a subject.

In some embodiments, the cell is a kidney cell (e.g. a podocyte) or a blood vessel cell (e.g. endothelial cell). In some embodiments, the cell comprises a mutant ApoL1 allele, wherein the mutant ApoL1 is as described herein. In some embodiments, the cell is characterized by overexpression of ApoL1 (mutant and/or wildtype). In some embodiments, the cell comprises an ApoL1 G1 mutant, an ApoL1 G1 mutant or both. In some embodiments, the cell selectively expresses a single ApoL1 mutant (either G1 or G2). In some embodiments, the cell expresses a plurality of ApoL1 mutants. In some embodiments, ApoL1 wildtype has sequence identical with NCBI gene ID 8542.

In some embodiments, selective expression comprises at least 80%, at least 85, at least 90%, at least 92%, at least 95%, at least 97%, at least 99% expression of a single ApoL1 mutant, wherein expression percentage relates to a fraction of the ApoL1 mutant of the total ApoL1 protein content.

In some embodiments, the method of the invention comprises selectively inhibiting or reducing ApoL1 G1 associated cell toxicity. In some embodiments, the method of the invention comprises selectively inhibiting or reducing ApoL1 G2 associated cell toxicity. In some embodiments, the method of the invention comprises inhibiting or reducing ApoL1 G1 and ApoL1 G2 associated cell toxicity.

In some embodiments, the method is for preventing or treating a kidney disease or disorder. In some embodiments, the method is for preventing or treating ApoL1 associated kidney disease or disorder. In some embodiments, ApoL1 associated kidney disease comprises hypertension-attributed kidney disease, sickle cell nephropathy, focal segmental glomerulosclerosis (FSGS), primary non-monogenic FSGS, HIV-associated nephropathy, lupus nephritis, end stage renal disease (ESRD), diabetic ESRD, albuminuria or any combination thereof. In some embodiments, the method is for preventing or treating ApoL1 associated cardiovascular disease. In some embodiments, ApoL1 is an ApoL1 mutant (such as ApoL1 G1 and/or ApoL1 G2).

In some embodiments, the method comprises administering the pharmaceutical composition of the invention at least 1 time, at least 2 times, at least 3 times, at least 4 times, at least 5 times, at least 7 times, or at least 10 times per day, or any value and range therebetween. Each possibility represents a separate embodiment of the invention. In some embodiments, the method comprises administering the composition or the combination of the invention 1-2 times per day, 1-3 times per day, 1-4 times per day, 1-5 times per day, 1-7 times per day, 2-3 times per day, 2-4 times per day, 2-5 times per day, 3-4 times per day, 3-5 times per day, or 5-7 times per day. Each possibility represents a separate embodiment of the invention.

In some embodiments, the subject is a mammal. In some embodiments, the subject is a lab animal. In some embodiments, the subject is a pet. In some embodiments, the subject is a rodent. In some embodiments, the subject is a farm animal. In some embodiments, the subject is a human subject.

In some embodiments, the composition of the present invention is administered in a therapeutically safe and effective amount. As used herein, the term "safe and effective amount" refers to the quantity of a component which is sufficient to yield a desired therapeutic response without undue adverse side effects, including but not limited to toxicity, such as calcemic toxicity, irritation, or allergic response, commensurate with a reasonable benefit/risk ratio when used in the presently described manner. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005).

In some embodiments, the effective amount or dose of the active ingredient can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages may vary depending on the dosage form employed and the route of administration utilized. In one embodiment, the exact formulation, route of administration and dosage can be chosen by the individual physician in view of the patient's condition. [See e.g., Goodman and Gilman's The Pharmacological Basis of Therapeutics, 13th Ed., McGraw-Hill/Education, New York, N.Y. (2017)].

In some embodiments, the subject is afflicted with a disease or disorder selected from the group comprising hypertension-attributed kidney disease, sickle cell nephropathy, and focal segmental glomerulosclerosis (FSGS), primary non-monogenic FSGS, HIV-associated nephropathy, lupus nephritis, ApoL1 associated cardiovascular disease end stage renal disease (ESRD), diabetic ESRD, albuminuria or any combination thereof.

In some embodiments, the subject is afflicted with ApoL1 associated cardiovascular disease or disorder. In some embodiments, the subject is afflicted with a kidney disease or disorder. In some embodiments, the subject is afflicted with a kidney disease or disorder characterized by a cell expressing at least one ApoL1 mutant. In some embodiments, the ApoL1 mutant is a translational product of a mutated ApoL1 gene. In some embodiments, a mutated ApoL1 gene comprises ApoL1G1 and/or ApoL1G2 mutation.

Figure 1B:
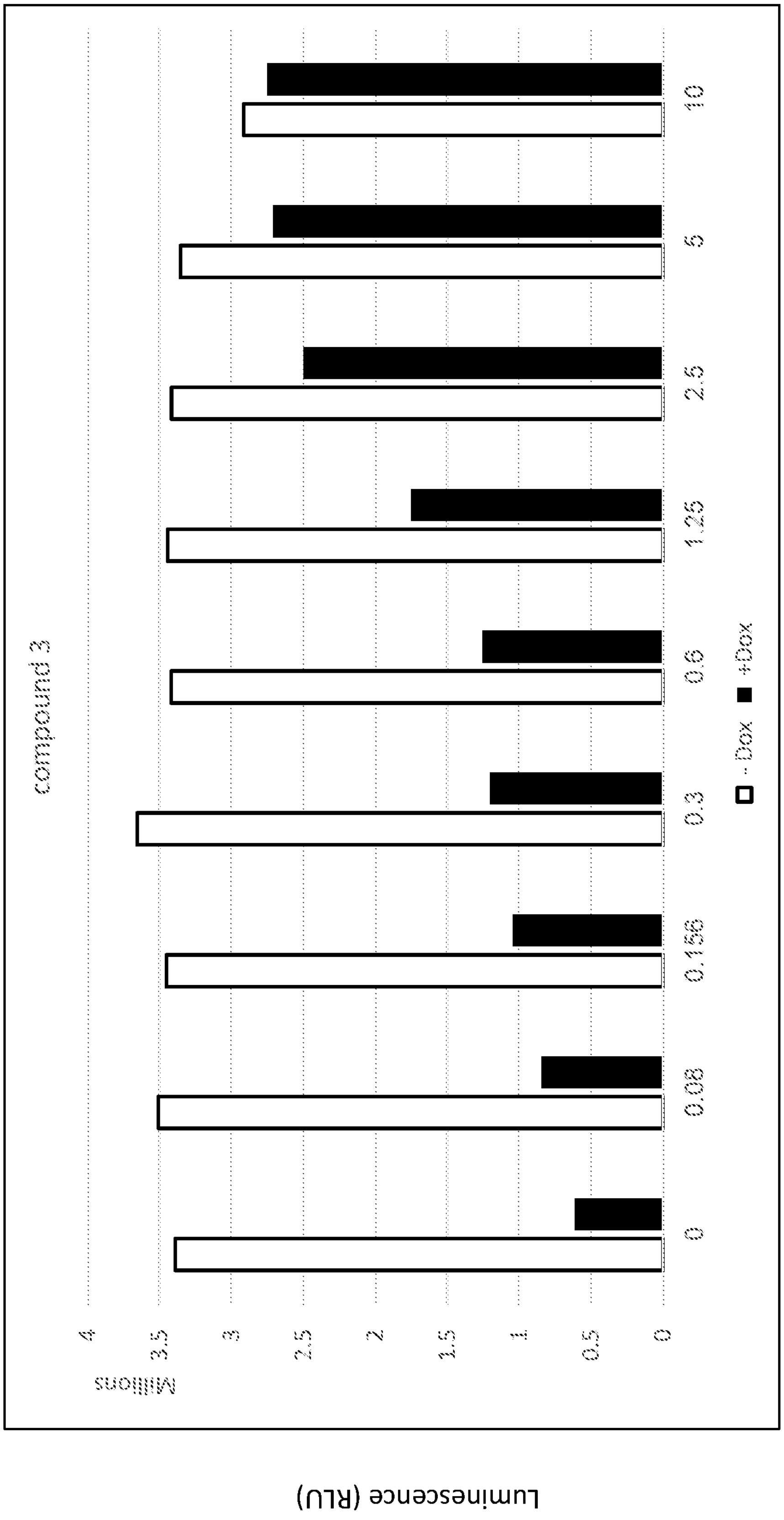
Figure 1C:
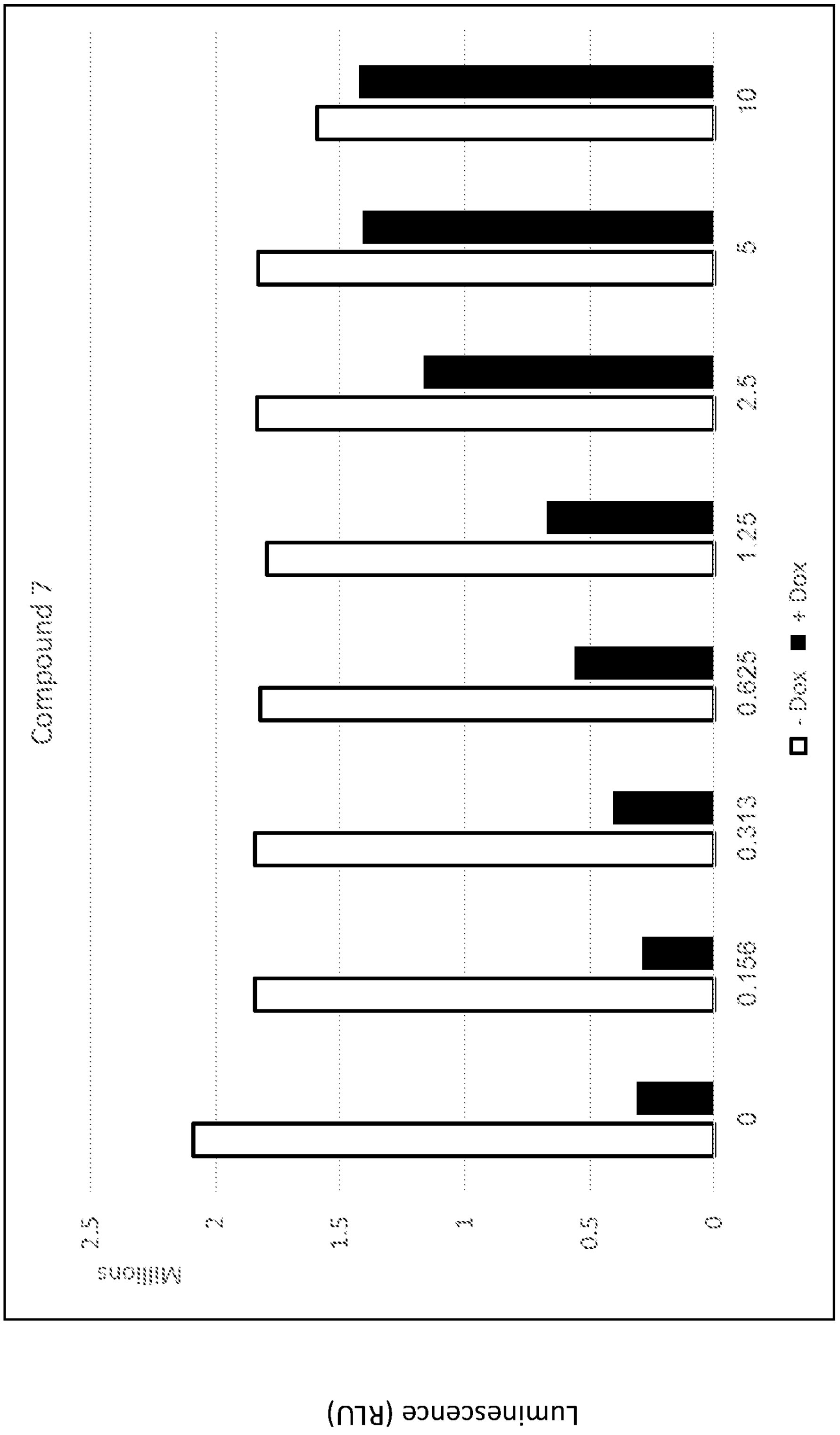

In some embodiments, reducing ApoL1 cell toxicity comprises at least 50%, at least 60%, at least 70%, at least 80%, at least 85%, at least 90%, at least 92%, at least 95%, at least 97%, at least 99% reduction of the cell death (such as by apoptosis, or by cell stress, or by protein interaction, or self-aggregation, or generation of aggregates) including any value therebetween. In some embodiments, the compound of the invention substantially reduces death rate of cells expressing an ApoL1 mutant, as represented by FIG. 1.

In some embodiments, the compound of the invention is substantially inactive with respect to the cells expressing a wild-type ApoL1 gene. In some embodiments, the method is for inhibiting enzymatic activity of the ApoL1 mutant.

In some embodiments, the compound of the invention has an increased affinity to the ApoL1 mutant as compared to the wild-type ApoL1, wherein the ApoL1 mutant is as described herein.

In some embodiments, the compound of the invention enhances cell viability of a cell expressing at least one ApoL1 mutant. In some embodiments, enhancement of cell viability is by at least 5 times, at least 10 times, at least 15 times, at least 20 times, at least 30 times, at least 30 times, at least 50 times, at least 80 times, at least 100 times, at least 200 times, at least 300 times, at least 400 times, at least 500 times, at least 700 times, at least 1000 times, at least 10,000 times, at least 50,000 times, at least 100,000 times as compared to untreated cells (as represented by FIG. 1). In some embodiments, the compound of the invention enhances viability of a cell expressing at least one ApoL1 mutant in a dose dependent manner (such as at a concentration between 0.2 and 10 μM).

In some embodiments, the compound of the invention is substantially non-toxic at a concentration of less than 15 μM, less than 12 μM, less than 11 μM, less than 10 μM, less than 9 μM, less than 8 μM, less than 6 μM, less than 5 μM, less than 3 μM, less than 1 μM, including any range or value therebetween.

In some embodiments, the compound of the invention is substantially non-toxic at a concentration between 0.001 and 15 μM, between 0.001 and 1 μM, between 1 and 5 μM, between 5 and 10 μM, between 10 and 12 μM, between 12 and 15 μM, including any range or value therebetween. In some embodiments, substantially comprises less than 20%, less than 17%, less than 15%, less than 13%, less than 10%, less than 8%, less than 5% cell death, including any range or value therebetween.

In some embodiments, ApoL1 gene mutation comprises ApoL1 G1 point mutation (S342G and/or I384M) and/or APOL1 G2 deletion mutation (Δ388N389Y). In some embodiments, the ApoL1 gene mutation is related to a resistance of a cell expressing ApoL1 mutant to trypanosomal infection.

In another aspect, there is provided a method for preventing or treating a proliferative disease comprising administering to the subject a therapeutically effective amount of the pharmaceutical composition or of the compound of the invention. In some embodiments, administering is by an oral administration, a topical administration, a systemic administration or a combination thereof. In some embodiments, administering is as described herein. In some embodiments, the method is for reducing cancer cell viability and/or arresting a proliferation thereof. In some embodiments, reducing is at least 50%, at least 60%, at least 70%, at least 80%, at least 85%, at least 90%, at least 92%, at least 95%, at least 97%, at least 99% reduction of the cell viability (such as by apoptosis, or by cell stress, or by protein interaction, or self-aggregation, or generation of aggregates, etc.).

In some embodiments, the subject is afflicted with a disease or disorder selected from the group comprising brain cancer, squamous cell cancer, bladder cancer, gastric cancer, pancreatic cancer, hepatic cancer, glioblastoma multiform breast cancer, head cancer, neck cancer, esophageal cancer, prostate cancer, colorectal cancer, lung cancer, renal cancer, kidney cancer, ovarian cancer, gynecological cancer, thyroid cancer, non-small cell lung cancer (NSCLC), refractory ovarian cancer, EGFR mutant related cancer and head and neck cancer or any combination thereof.

Carrier

In some embodiments, the pharmaceutical composition of the invention comprises a therapeutically effective amount of the compound of the invention and a pharmaceutically acceptable carrier. In some embodiments, the pharmaceutically acceptable salt comprises the compound of the invention and the pharmaceutically acceptable anion. In some embodiments, the pharmaceutical composition comprises a therapeutically effective amount of the compound of the invention as an active ingredient. In some embodiments, the compound of the invention as the only active ingredient within the pharmaceutical composition of the invention.

Non-limiting examples of pharmaceutically acceptable anions include but are not limited to: acetate, aspartate, benzenesulfonate, benzoate, bicarbonate, carbonate, halide (such as bromide, chloride, iodide, and fluoride), bitartrate, citrate, salicylate, stearate, succinate, sulfate, tartrate, decanoate, fumarate, gluconate, and lactate or any combination thereof.

For example, the term "pharmaceutically acceptable" can mean approved by a regulatory agency of the Federal or a state government or listed in the U.S. Pharmacopeia or other generally recognized pharmacopeia for use in animals, and more particularly in humans.

In some embodiments, the pharmaceutical composition as described herein is a topical composition. In some embodiments, the pharmaceutical composition is an oral composition. In some embodiments, the pharmaceutical composition is an injectable composition. In some embodiments, the pharmaceutical composition is for a systemic use.

In some embodiments, the pharmaceutical composition is any of an emulsion, a liquid solution, a gel, a paste, a suspension, a dispersion, an ointment, a cream or a foam.

As used herein, the term "carrier" refers to a diluent, adjuvant, excipient, or vehicle with which the active ingredient is administered. Such carriers can be sterile liquids, such as water-based and oils, including those of petroleum, animal, vegetable or synthetic origin, such as peanut oil, soybean oil, mineral oil, sesame oil and the like, polyethylene glycols, glycerin, propylene glycol or other synthetic solvents.

Other non-limiting examples of carriers include, but are not limited to: terpenes derived from Cannabis, or total terpene extract from Cannabis plants, terpenes from coffee or cocoa, mint-extract, eucalyptus-extract, citrus-extract, tobacco-extract, anise-extract, any vegetable oil, peppermint oil, d-limonene, b-myrcene, a-pinene, linalool, anethole, a-bisabolol, camphor, b-caryophyllene and caryophyllene oxide, 1,8-cineole, citral, citronella, delta-3-carene, farnesol, geraniol, indomethacin, isopulegol, linalool, unalyl acetate, b-myrcene, myrcenol, 1-menthol, menthone, menthol and neomenthol, oridonin, a-pinene, diclofenac, nepafenac, bromfenac, phytol, terpineol, terpinen-4-ol, thymol, and thymoquinone. One skilled in the art will appreciate, that a particular carrier used within the pharmaceutical composition of the invention may vary depending on the route of administration.

In some embodiments, the carrier improves the stability of the active ingredient in a living organism. In some embodiments, the carrier improves the stability of the active ingredient within the pharmaceutical composition. In some embodiments, the carrier enhances the bioavailability of the active ingredient.

Water may be used as a carrier such as when the active ingredient has a sufficient aqueous solubility, so as to be administered intravenously. Saline solutions and aqueous dextrose and glycerol solutions can also be employed as liquid carriers, particularly for injectable solutions.

In some embodiments, the carrier is a liquid carrier. In some embodiments, the carrier is an aqueous carrier.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned. The carrier may comprise, in total, from 0.1% to 99.99999% by weight of the composition/s or the pharmaceutical composition/s presented herein.

In some embodiments, the pharmaceutical composition includes incorporation of any one of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions may influence the physical state, solubility, stability, rate of in vivo release, and rate of in vivo clearance.

In some embodiments, the pharmaceutical composition is a liquid at a temperature between 15 to 45° C. In some embodiments, the pharmaceutical composition is a solid at a temperature between 15 to 45° C. In some embodiments, the pharmaceutical composition is a semi-liquid at a temperature between 15 to 45° C. It should be understood that the term "semi-liquid", is intended to mean materials which are flowable under pressure and/or shear force. In some embodiments, semi-liquid compositions include creams, ointments, gel-like materials and other similar materials. In some embodiments, the pharmaceutical composition is a semi-liquid composition, characterized by a viscosity in a range from 31,000-800,000 cps.

Non-limiting examples of carriers for pharmaceutical compositions being in the form of a cream include but are not limited to: non-ionic surfactants (e.g., glyceryl monolinoleate glyceryl monooleate, glyceryl monostearate lanolin alcohols, lecithin mono- and di-glycerides poloxamer polyoxyethylene 50 stearate, and sorbitan trioleate stearic acid), anionic surfactants (e.g. pharmaceutically acceptable salts of fatty acids such as stearic, oleic, palmitic, and lauric acids), cationic surfactants (e.g. pharmaceutically acceptable quaternary ammonium salts such as benzalkonium chloride, benzethonium chloride, and cetylpyridinium chloride) or any combination thereof.

In some embodiments, the pharmaceutical composition being in the form of a cream further comprises a thickener.

Non-limiting examples of thickeners include, but are not limited to microcrystalline cellulose, a starch, a modified starch, gum tragacanth, gelatin, and a polymeric thickener (e.g. polyvinylpyrrolidone) or any combination thereof.

In some embodiments, the pharmaceutical composition comprising the compound of the invention is in a unit dosage form. In some embodiments, the pharmaceutical composition is prepared by any of the methods well known in the art of pharmacy. In some embodiments, the unit dosage form is in the form of a tablet, capsule, lozenge, wafer, patch, ampoule, vial or pre-filled syringe.

In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems. In some embodiments, the effective dose is determined as described hereinabove.

In another embodiment, the pharmaceutical composition of the invention is administered in any conventional oral, parenteral or transdermal dosage form.

As used herein, the terms "administering", "administration", and like terms refer to any method which, in sound medical practice, delivers a composition containing an active agent to a subject in such a manner as to provide a therapeutic effect.

In some embodiments, the pharmaceutical composition is administered via oral (i.e., enteral), rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. In addition, it may be desirable to introduce the pharmaceutical composition of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

In some embodiments, the pharmaceutical composition is in a form of, for example, and not by way of limitation, an ointment, cream, gel, paste, foam, aerosol, suppository, pad or gelled stick.

In some embodiments, for oral applications, the pharmaceutical composition or is in the form of a tablets or a capsule, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. In some embodiments, the tablet of the invention is further film coated. In some embodiments, oral application of the pharmaceutical composition or of the kit is in a form of a drinkable liquid. In some embodiments, oral application of the pharmaceutical composition or of the kit is in a form of an edible product.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

In some embodiments, the subject is a mammal. In some embodiments, the subject is a lab animal. In some embodiments, the subject is a pet. In some embodiments, the subject is a rodent. In some embodiments, the subject is a farm animal. In some embodiments, the subject is a human subject.

In some embodiments, compositions including the preparation of the present invention formulated in a compatible pharmaceutical carrier are prepared, placed in an appropriate container, and labeled for treatment of an indicated condition.

In some embodiments, compositions of the present invention are presented in a pack or dispenser device, such as an FDA approved kit, which contains, one or more unit dosages forms containing the active ingredient. In some embodiments, the pack, for example, comprises metal or plastic foil, such as a blister pack. In some embodiments, the pack or dispenser device is accompanied by instructions for administration. In some embodiments, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in some embodiments, is labeling approved by the U.S. Food and Drug Administration for prescription drugs or of an approved product insert.

Definitions

As used herein, the term "alkyl" describes an aliphatic hydrocarbon including straight chain and branched chain groups. Preferably, the alkyl group has between 1 to 10 carbon atoms, and more preferably 1-6 carbon atoms (or $C_1$-$C_6$ alkyl). A short alkyl therefore has 20 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl. As used herein the term "$C_1$-$C_6$ alkyl" including any $C_1$-$C_6$ alkyl related compounds, is referred to any linear or branched alkyl chain comprising between 1 and 6, between 1 and 2, between 2 and 3, between 3 and 4, between 4 and 5, between 5 and 6, carbon atoms, including any range therebetween. In some embodiments, $C_1$-$C_6$ alkyl comprises any of methyl, ethyl, propyl, butyl, pentyl, iso-pentyl, hexyl, and tert-butyl or any combination thereof. In some embodiments, $C_1$-$C_6$ alkyl as described herein further comprises an unsaturated bond, wherein the unsaturated bond is located at $1^{st}$ $2^{nd}$, $3^{rd}$, $4^{th}$, $5^{th}$, $6^{th}$ position of the $C_1$-$C_6$ alkyl.

As used herein the term "$C_1$-$C_{10}$ alkyl" including any $C_1$-$C_6$ alkyl related compounds, is referred to any linear or branched alkyl chain comprising between 1 and 6, between 1 and 2, between 2 and 3, between 3 and 4, between 4 and 5, between 5 and 6, between 6 and 8, between 8 and 10, carbon atoms, including any range therebetween. In some embodiments, $C_1$-$C_{10}$ alkyl comprises any of methyl, ethyl, propyl, butyl, pentyl, iso-pentyl, hexyl, nonyl, decyl, ethenyl, propenyl, butenyl, and tert-butyl, or any combination thereof, wherein each alkyl is optionally substituted by one or more substituents, as described herein.

In some embodiments, $C_1$-$C_{10}$ alkyl as described herein further comprises an unsaturated bond, wherein the unsaturated bond is located at $1^{st}$ $2^{nd}$, $3^{rd}$, $4^{th}$, $5^{th}$, $6^{th}$, $7^{th}$, $8^{th}$, $9^{th}$ or $10^{th}$ position of the $C_1$-$C_{10}$) alkyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein. In some embodiments, the term "cycloalkyl" refers to a C3-C10 cyclic ring. In some embodiments, the term "cycloalkyl" refers to a C3-C10 cyclic ring comprising 1, 2, 3, or 4 heteroatoms (e.g. N, NH, O, or S). ($C_3$-$C_{10}$) ring is referred to an optionally substituted C3, C4, C5, C6, C7, C8, C9 or C10 ring. In some embodiments, ($C_3$-$C_{10}$) ring comprises optionally substituted cyclopropane, cyclobutene, cyclopentane, cyclohexane, or cycloheptane.

In some embodiments, the term "cycloalkyl" refers to a group containing a non-aromatic ring wherein each of the atoms forming the ring is a carbon atom. Cycloalkyls can be formed by three, four, five, six, seven, eight, nine, or more than nine carbon atoms. Cycloalkyls can be optionally substituted. In certain embodiments, a cycloalkyl contains one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane and cycloheptene.

In some embodiments, the term "aryl" describes an all-carbon monocyclic or fused-ring polycyclic (i.e. rings which share adjacent pairs of carbon atoms) groups having a completely conjugated pi-electron system. In some embodiments, the term "aryl" describes an aromatic ($C_6$-$C_{12}$) ring. The aryl group may be substituted or unsubstituted, as indicated herein. In some embodiments, the term "($C_6$-$C_{12}$) ring" is referred to an optionally substituted C6, C7, C8, C9, C10, C11, or C12 aromatic ring. In some embodiments, ($C_6$-$C_{12}$) aromatic ring is referred to a bicyclic aryl or bicyclic heteroaryl (e.g. fused ring, spirocyclic ring, and biaryl ring). In some embodiments, the term "aryl" refers to a monocyclic, bicyclic or tricyclic aromatic system that contains no ring heteroatoms. Where the systems are not monocyclic, the term aryl includes for each additional ring the saturated form (perhydro form) or the partially unsaturated form (for example the dihydro form or tetrahydro form) or the maximally unsaturated (nonaromatic) form. In some embodiments, the term aryl refers to bicyclic radicals in which the two rings are aromatic and bicyclic radicals in which only one ring is aromatic. Examples of aryl include phenyl, naphthyl, anthracyl, indanyl, 1,2-dihydro-naphthyl, 1,4-dihydronaphthyl, indenyl, 1,4-naphthoquinonyl and 1,2,3,4-tetrahydronaphthyl.

Aryl rings can be formed by three, four, five, six, seven, eight, nine, or more than nine carbon atoms. In some embodiments, aryl refers to a 3-, 4-, 5-, 6-, 7-, 8-, 9-, 10-, 11-, 12-, 13- or 14-membered, aromatic mono-, bi- or tricyclic system. In some embodiments, aryl refers to an aromatic $C_3$-$C_9$ ring. In some embodiments, aryl refers to an aromatic $C_4$-$C_8$ ring. Aryl groups can be optionally substituted.

As used herein the term "bicyclic heteroaryl" referred to ($C_6$-$C_{12}$) a bicyclic heteroaryl ring, wherein bicyclic ($C_6$-$C_{10}$) ring is as described herein.

As used herein the term "bicyclic aryl" referred to ($C_6$-$C_{12}$) a bicyclic aryl ring, wherein bicyclic ($C_6$-$C_{12}$) ring is as described herein.

The term "alkoxy" describes both an O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, nitro, amino, hydroxyl, thiol, thioalkoxy, carboxy, amide, aryl and aryloxy, depending on the substituted group and its position in the molecule. Additional substituents are also contemplated.

The term "haloalkyl" describes an alkyl group as defined herein, further substituted by one or more halide(s).

The term "haloalkoxy" describes an alkoxy group as defined herein, further substituted by one or more halide(s).

The term "hydroxyl" or "hydroxy" describes a —OH group.

The term "mercapto" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amino" describes a —NR'R" group, with R' and R" as described herein.

As used herein, the term "heterocycle" refers to a ring wherein at least one atom forming the ring is a carbon atom and at least one atom forming the ring is a heteroatom. Heterocyclic rings can be formed by three, four, five, six, seven, eight, nine, or more than nine atoms. Any number of those atoms can be heteroatoms (i.e., a heterocyclic ring can contain one, two, three, four, five, six, seven, eight, nine, or more than nine heteroatoms, provided that at least one atom in the ring is a carbon atom). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocyclic ring will have additional heteroatoms in the ring. Designations such as "4-6 membered heterocycle" refer to the total number of atoms that comprise the ring (i.e., a four, five, or six membered ring, in which at least one atom is a carbon atom, at least one atom is a heteroatom and the remaining two to four atoms are either carbon atoms or heteroatoms). In heterocycles containing two or more heteroatoms, those two or more heteroatoms can be the same or different from one another. Heterocycles can be optionally substituted. Binding to a heterocycle can be at a heteroatom or via a carbon atom. As used herein, the term "carbocycle" refers to a ring, where each of the atoms forming the ring is a carbon atom. Carbocyclic rings can be formed by 3, 4, 5, 6, 7, 8, 9, or more than 9 carbon atoms. Carbocycles can be optionally substituted.

As used herein, the term "heteroatom" refers to an atom other than carbon or hydrogen. Heteroatoms are typically independently selected from oxygen, sulfur, nitrogen and phosphorus, but are not limited to those atoms. In embodiments in which two or more heteroatoms are present, the two or more heteroatoms can all be the same as one another, or some or all of the two or more heteroatoms can each be different from the others.

As used herein, the term "bicyclic ring" refers to two rings, where the two rings are fused. Bicyclic rings include, e.g., decaline, pentalene, indene, naphthalene, azulene, heptalene, isobenzofuran, chromene, indolizine, isoindole, indole, indoline, purine, quinolizine, isoquinoline, quinoline, phthalazine, naphthyrididine, quinoxaline, cinnoline, pteridine, isochroman, chroman and various hydrogenated derivatives thereof. Bicyclic rings can be optionally substituted. Each ring is independently aromatic or non-aromatic. In certain embodiments, both rings are aromatic. In certain embodiments, both rings are non-aromatic. In certain embodiments, one ring is aromatic, and one ring is non-aromatic.

As used herein, the term "aromatic" refers to a planar ring having a delocalized π-electron system containing 4n+2 π electrons, where n is an integer. Aromatic rings can be formed by five, six, seven, eight, nine, or more than nine atoms. Aromatics optionally can be substituted. Examples of aromatic groups include, but are not limited to, phenyl, tetralinyl, naphthalenyl, phenanthrenyl, anthracenyl, fluorenyl, indenyl and indanyl. The teem aromatic includes, e.g., benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoro-methyl. In certain embodiments, an aromatic group is substituted at one or more of the para, meta, and/or ortho positions. Examples of aromatic groups containing substitutions include, but are not limited to, phenyl, 3-halophenyl, 4-halophenyl, 3-hydroxyphenyl, 4-hydroxy-phenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyano-phenyl, 4-cyanophenyl, naphthyl, dimethylphenyl, hydroxynaphthyl, hydroxymethyl-phenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl and 4-(2-oxopyrrolidin-1-yl)phenyl.

The term "carboxy" or "carboxyl" describes a —C(O)OR' group, where R' is hydrogen, alkyl, cycloalkyl, alkenyl, aryl, heteroaryl (bonded through a ring carbon) or heterocyclyl (bonded through a ring carbon) as defined herein, or wherein R' is absent, e.g. carboxylate salt.

The term "carbonyl" describes a —C(O)R' group, where R' is as defined hereinabove.

The above-terms also encompass thio-derivatives thereof (thiocarboxy and thiocarbonyl).

The term "carboxylic acid derivative" as used herein encompasses carboxy, amide, carbonyl, anhydride, carbonate ester, and carbamate, as described herein.

The term "thiocarbonyl" describes a —C(S)R' group, where R' is as defined hereinabove.

A "thiocarboxy" group describes a —C(S)OR' group, where R' is as defined herein.

A "sulfinyl" group describes an —S(O)R' group, where R' is as defined herein.

A "sulfonyl" or "sulfonate" group describes an $—S(O)_2R'$ group, where R' is as defined herein.

A "carbamoyl" or "carbamate" group describes an —OC(O)NR'R" group, where R' is as defined herein and R" is as defined for R'.

A "nitro" group refers to a $—NO_2$ group.

In some embodiments, the term "amide" refers to a chemical moiety with formula —(R)n—C(O)NHR' or —(R)n—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide can be an amino acid or a peptide.

The term "amide" as used herein encompasses C-amide and N-amide.

The term "C-amide" describes a —C(O)NR'R" end group or a —C(O)NR'-linking group, as these phrases are defined hereinabove, where R' and R" are as defined herein.

The term "N-amide" describes a —NR"C(O)R' end group or a —NR'C(O)— linking group, as these phrases are defined hereinabove, where R' and R" are as defined herein.

The term "carboxylic acid derivative" as used herein encompasses carboxy, amide, carbonyl, anhydride, carbonate ester, and carbamate.

A "cyano" or "nitrile" group refers to a —CN group.

The term "azo" or "diazo" describes an —N═NR' end group or an —N═N— linking group, as these phrases are defined hereinabove, with R' as defined hereinabove.

The term "guanidine" describes a —R'NC(N)NR"R'" end group or a —R'NC(N) NR"— linking group, as these phrases are defined hereinabove, where R', R" and R'" are as defined herein.

As used herein, the term "alkylsulfate" refers to an alkyl group as defined herein, further substituted by one or more sulfate groups ($—OS(═O)_2OH$, and/or ($—OS(═O)_2O—$).

As used herein, the term "azide" refers to a —N3 group.

The term "sulfonamide" refers to a $—S(O)_2NR'R"$ group, with R' and R" as defined herein.

The term "phosphonyl" or "phosphonate" describes an $—OP(O)—(OR')_2$ group, with R' as defined hereinabove.

The term "phosphinyl" describes a —PR'R" group, with R' and R" as defined hereinabove.

The term "alkylaryl" describes an alkyl, as defined herein, which substituted by an aryl, as described herein. An exemplary alkylaryl is benzyl.

As used herein, the term "heteroaryl" refers to an aromatic ring in which at least one atom forming the aromatic ring is a heteroatom. Heteroaryl rings can be foamed by three, four, five, six, seven, eight, nine and more than nine atoms. Heteroaryl groups can be optionally substituted. Examples of heteroaryl groups include, but are not limited to, aromatic $C_{3-8}$ heterocyclic groups containing one oxygen or sulfur atom, or two oxygen atoms, or two sulfur atoms or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl is selected from among oxazolyl, isoxazolyl, oxadiazolyl, thiazolyl, isothiazolyl, pyridinyl, pyridazinyl, pyrimidinal, pyrazinyl, indolyl, benzimidazolyl, quinolinyl, isoquinolinyl, quinazolinyl or quinoxalinyl.

In some embodiments, a heteroaryl group is selected from among pyrrolyl, furanyl (furyl), thiophenyl (thienyl), imidazolyl, pyrazolyl, 1,2,3-triazolyl, 1,2,4-triazolyl, 1,3-oxazolyl (oxazolyl), 1,2-oxazolyl (isoxazolyl), oxadiazolyl, 1,3-thiazolyl (thiazolyl), 1,2-thiazolyl (isothiazolyl), tetrazolyl, pyridinyl (pyridyl)pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, benzodioxolyl, acridinyl, quinolinyl, isoquinolinyl, quinazolinyl, quinoxalinyl, phthalazinyl, thienothiophenyl, 1,8-naphthyridinyl, other naphthyridinyls, pteridinyl or phenothiazinyl. Where the heteroaryl group includes more than one ring, each additional ring is the saturated form (perhydro form) or the partially unsaturated form (e.g., the dihydro form or tetrahydro form) or the maximally unsaturated (nonaromatic) form. The term heteroaryl thus includes bicyclic radicals in which the two rings are aromatic and bicyclic radicals in which only one ring is aromatic. Such examples of heteroaryl are include 3H-indolinyl, 2(1H)-quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydro-isoquinolinyl, chromonyl, 3,4-dihydroiso-quinoxalinyl, 4-(3H) quinazolinonyl, 4H-chromenyl, 4-chromanonyl, oxindolyl, 1,2,3,4-tetrahydroisoquinolinyl, 1,2,3,4-tetrahydro-quinolinyl, 1H-2,3-dihydroisoindolyl, 2,3-dihydrobenzo[f]isoindolyl, 1,2,3,4-tetrahydrobenzo-[g]isoquinolinyl, 1,2,3,4-tetrahydro-benzo[g]isoquinolinyl, chromanyl, isochromanonyl, 2,3-dihydrochromonyl, 1,4-benzo-dioxanyl, 1,2,3,4-tetrahydro-quinoxalinyl, 5,6-dihydro-quinolyl, 5,6-dihydroisoquinolyl, 5,6-dihydroquinoxalinyl, 5,6-dihydroquinazolinyl, 4,5-dihydro-1H-benzimidazolyl, 4,5-dihydro-benzoxazolyl, 1,4-naphthoquinolyl, 5,6,7,8-tetrahydro-quinolinyl, 5,6,7,8-tetrahydro-isoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydro-benzoxazolyl, 1H-4-oxa-1,5-diazanaphthalen-2-onyl, 1,3-dihydroimidizolo-[4,5]-pyridin-2-onyl, 2,3-dihydro-1,4-dinaphtho-quinonyl, 2,3-dihydro-1H-pyrrol[3,4-b]quinolinyl, 1,2,3,4-tetrahydrobenzo[b]-[1,7] naphthyridinyl, 1,2,3,4-tetra-hydrobenz[b][1,6]-naphthyridinyl, 1,2,3,4-tetrahydro-9H-pyrido[3,4-b]indolyl, 1,2,3,4-tetrahydro-9H-pyrido[4,3-b]indolyl, 2,3-dihydro-1H-pyrrolo-[3,4-b]indolyl, 1H-2,3,4,5-tetrahydro-azepino [3,4-b]indolyl, 1H-2,3,4,5-tetrahydroazepino-[4,3-b]indolyl, 1H-2,3,4,5-tetrahydro-azepino[4,5-b]indolyl, 5,6,7,8-tetrahydro[1,7]napthyridinyl, 1,2,3,4-tetrahydro-[2,7]-naphthyridyl, 2,3-dihydro[1,4]dioxino[2,3-b]pyridyl, 2,3-dihydro[1,4]-dioxino[2,3-b]pryidyl, 3,4-dihydro-2H-1-oxa [4,6]diaz anaphthalenyl, 4,5,6,7-tetrahydro-3H-imidazo-[4,5-c]pyridyl, 6,7-dihydro[5,8]diazanaphthalenyl, 1,2,3,4-tetrahydro[1,5]-napthyridinyl, 1,2,3,4-tetrahydro[1,6] napthyridinyl, 1,2,3,4-tetrahydro[1,7]napthyridinyl, 1,2,3,4-tetrahydro-[1,8]napthyridinyl or 1,2,3,4-tetrahydro[2,6] napthyridinyl. In some embodiments, heteroaryl groups are optionally substituted. In one embodiment, the one or more substituents are each independently selected from among halo, hydroxy, amino, cyano, nitro, alkylamido, acyl, $C_{1-6}$-alkyl, $C_{1-6}$-haloalkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl.

Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline and quinoxaline. In some embodiments, the substituents are halo, hydroxy, cyano, O—$C_{1-6}$-alkyl, $C_{1-6}$-alkyl, hydroxy-$C_{1-6}$-alkyl and amino-$C_{1-6}$-alkyl.

In some embodiments, the terms "heteroaryl" and "C5-C6 heteroaryl" are used herein interchangeably.

As used herein, the terms "halo" and "halide", which are referred to herein interchangeably, describe an atom of a halogen, that is fluorine, chlorine, bromine, or iodine, also referred to herein as fluoride, chloride, bromide, and iodide.

The term "haloalkyl" describes an alkyl group as defined above, further substituted by one or more halide(s).

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings can be optionally substituted. Rings can form part of a ring system.

As used herein, the term "ring system" refers to two or more rings, wherein two or more of the rings are fused. The term "fused" refers to structures in which two or more rings share one or more bonds.

The term "substituted" or the term "substituent" is referred to 1, 2, 3, 4 or 5 substituents, wherein each substituent is independently selected from $(C_0-C_6)$alkyl-aryl, $(C_0-C_6)$alkyl-heteroaryl, $(C_0-C_6)$alkyl-$(C_3-C_8)$ cycloalkyl, optionally substituted $C_3-C_8$ heterocyclyl, halogen, $NO_2$, CN, OH, $CONH_2$, $CONR_2$, $CNNR_2$, $CSNR_2$, CONH—OH, CONH—$NH_2$, NHCOR, NHCSR, NHCNR, —NC(=O)OR, —NC(=O)NR, —NC(=S)OR, —NC(=S)NR, $SO_2R$, SOR, —SR, $SO_2OR$, $SO_2N(R)_2$, —$NHNR_2$, —NNR, $C_1-C_6$ haloalkyl, optionally substituted $C_1-C_6$ alkyl, $NH_2$, NH($C_1-C_6$ alkyl), N($C_1-C_6$ alkyl)$_2$, $C_1-C_6$ alkoxy, $C_1-C_6$ haloalkoxy, hydroxy($C_1-C_6$ alkyl), hydroxy ($C_1-C_6$ alkoxy), alkoxy($C_1-C_6$ alkyl), alkoxy($C_1-C_6$ alkoxy), $C_1-C_6$ alkyl$NR_2$, $C_1-C_6$ alkyl SR, CONH($C_1-C_6$ alkyl), CON ($C_1-C_6$ alkyl)$_2$, $CO_2H$, $CO_2R$, —OCOR, —OCOR, —OC(=O)OR, —OC(=O)NR, —OC(=S)OR, —OC(=S)NR, including nay combination thereof.

General

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "substantially" refers at least 60%, at least 70%, at least 80%, at least 85%, at least 90%, at least 95%, at least 97%, at least 99%, at least 99.9%, including any rage or value therebetween. In some embodiments, the terms "substantially" and the term "consisting essentially of" are used herein interchangeably.

In some embodiments, the terms "treatment" or "treating" of a disease, disorder, or condition encompasses substantial alleviation of at least one symptom thereof, substantial reduction in the severity thereof, or inhibition of the progression thereof, wherein substantial is as described herein. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described active ingredients prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of inflammatory disorders.

The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression.

Conversely, the term "treatment" refers to the clinical application of active agents to combat an already existing condition whose clinical presentation has already been realized in a patient.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include", and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Unless specifically stated or obvious from context, as used herein, the term "or" is understood to be inclusive.

Throughout this specification and claims, the word "comprise" or variations such as "comprises" or "comprising" indicate the inclusion of any recited integer or group of integers but not the exclusion of any other integer or group of integers.

As used herein, the term "consists essentially of" or variations such as "consist essentially of" or "consisting essentially of" as used throughout the specification and claims, indicate the inclusion of any recited integer or group of integers, and the optional inclusion of any recited integer or group of integers that do not materially change the basic or novel properties of the specified method, structure or composition.

As used herein, the terms "comprises", "comprising", "containing", "having" and the like can mean "includes", "including", and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In one embodiment, the terms "comprises" "comprising", and "having" are/is interchangeable with "consisting".

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

EXAMPLES

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Generally, the nomenclature used herein, and the laboratory procedures utilized in the present invention include molecular, biochemical, and microbiological techniques. Such techniques are thoroughly explained in the literature.

Materials and Methods

Compound 1 was purchased from MayBridge (Cat. HTS12305) and compounds 3 and 7 from ChemBridge (Cat. 7990186, 37031742, respectively). Compound solutions were prepared by diluting a stock solution (10 mM in 100% DMSO) with water to obtain a desired concentration prior to use.

ApoL1-G1-induced T-REx-293 stable cell line was generated by introducing Flag-tagged human G1 ApoL1 variant DNA (with African genomic sequence background) into the pcDNA4/TO plasmid, which yield expression upon Doxycycline addition. Cells were cultured in DMEM (Gibco, 41965-039) supplemented with 10% FBS, 1% penicillin-streptomycin at 37° C.

In order to estimate the effect of compounds 1, 3 and 7 on ApoL1-induced cells a cell viability assay was performed as following: cells were seeded at density 23K cells per well (96-well plate). Prior to seeding, wells were coated with Fibronectin (Biological industries, 03-090-1-05) for 1 hour at 37° C. On the following day, cells were switched to the same growth medium but containing 1 ng/ml Doxycycline (Sigma, D9891) with different concentrations of compounds 1, 3 or 7, for 16 hours. Then, cells were subjected to viability assay according to manufacturer's instructions, using Cell-Titer-Glo luminescent cell viability assay kit (Promega, G7570). The plate was read using Infinite 200 PRO for luminescence, which indicated live-cell count.

Example 1

ApoL1-G1-Induced Cell Viability Assay

Induction of ApoL1-G1 variant by doxycycline causes toxicity in T-REx-293 cell line. In order to identify potential inhibitors of ApoL1 toxicity, a cell-based high throughput screening of 200,000 chemical compounds was performed. Cells were incubated with a compound solution (at 10 μM concentration). After a detailed screening, three compounds (compounds 1, 3 and 7, the chemical structures are as described hereinabove) showed the highest cell protective effect, without exhibiting a significant cell toxicity.

As represented by FIG. 1, compounds 1, 3 and 7 showed a concentration dependent viability increase of ApoL1-G1 expressing cells (orange bars). Blue bars represent viability of cells expressing wild type ApoL1. Additional compounds are tested in order to evaluate cell protective effect thereof.

Example 2

Cell Proliferation Inhibition Induced by Exemplary Compounds of the Invention

The inventors performed cell toxicity assay, in order to evaluate a potential anti-proliferative effect of exemplary compounds of the invention.

T-REx-293 cells were seeded at a density of 25K cells/well on fibronectin in 96-well plates and grown in DMEM with 10% FBS, 1% P/S medium. 24 hours post-seeding medium was changed to a fresh medium comprising the tested compounds (KS-1, KS-2, or KS-8) at a concentration of 5-10 μM. Non-treated cells were used as a negative control. After 16 hours one plate of the cells was taken for cell viability test using Cell-Titer Glo reagent (Promega). Cells on the other plate were imaged using Incucyte ZOOM system.

The tested exemplary compounds of the invention were as follows:

KS-1

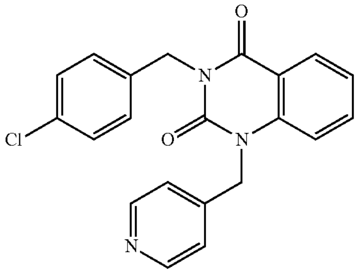

KS-2

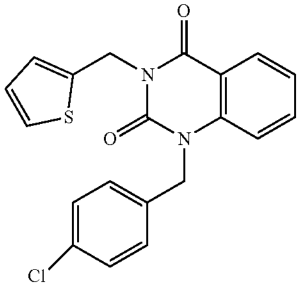

KS-8

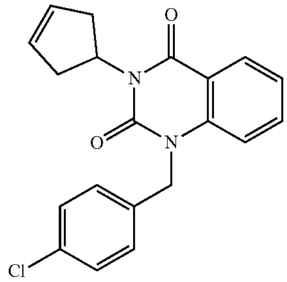

Figure 2:
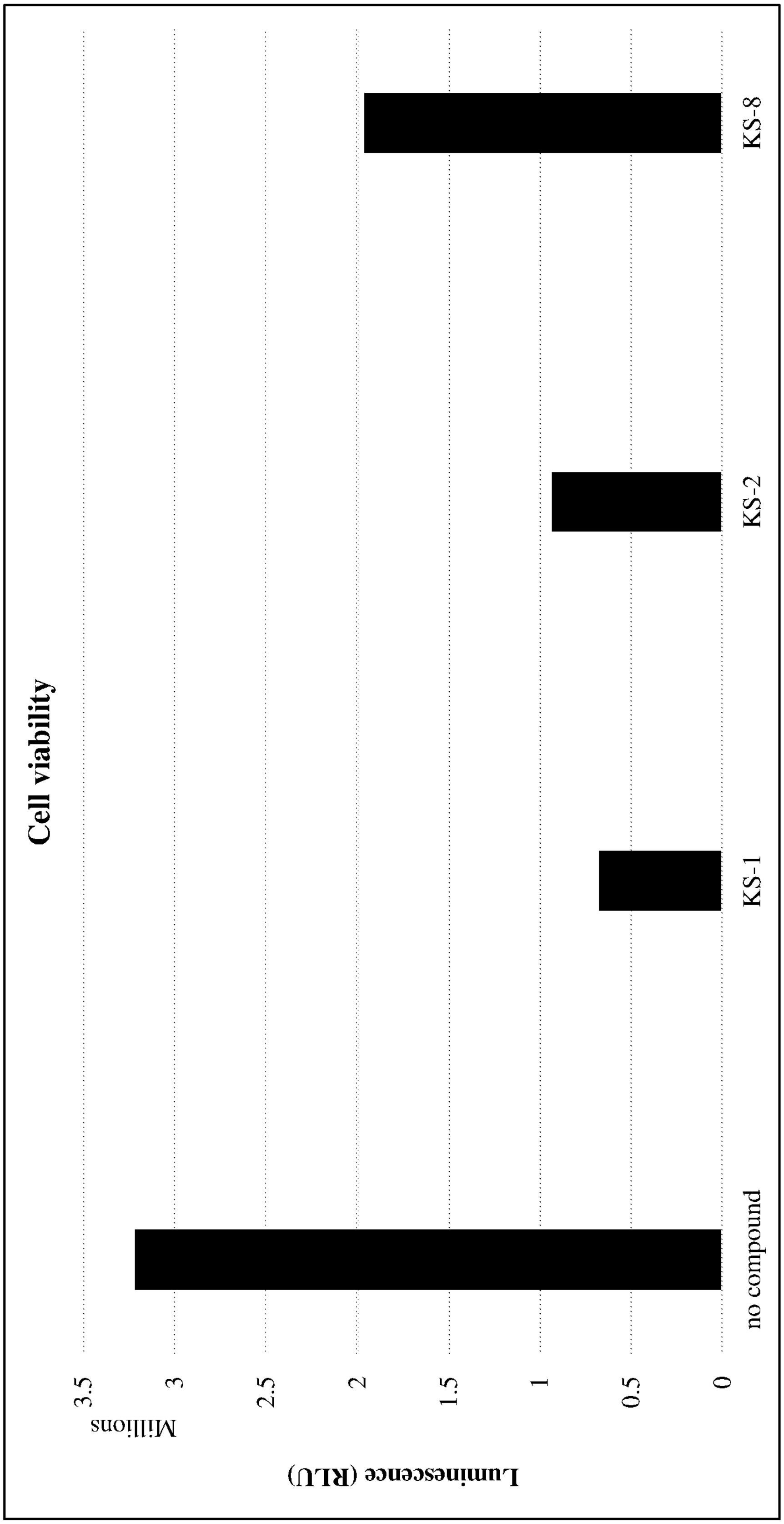
FIG. 2 is a bar graph representing viability of T-REx-293 cells after 16 hours incubation with exemplary compound of the invention (KS-1, KS-2, or KS-8 at a concentration of 10 μM), versus non-treated cells (as a negative control). Y axis depicts cell count.

The results are summarized in FIG. 2 (for 10 μM concentration). As can be seen from the graph represented in FIG. 2, the cell count determined via a luminescence signal (relative light units, RLU) was lower for the cells grown in the presence of the compounds KS-1, KS-2 and KS-8. Accordingly, the tested compounds significantly reduced viability and/or proliferation rate of the immortalized cells. It is assumed, that compounds of the invention might be utilized as potent anti-proliferative agents.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for treating ApoL1 associated kidney disease comprising administering to a subject in need thereof a therapeutically effective amount of a compound or a pharmaceutically acceptable salt thereof, wherein the compound is represented by Formula 1D:

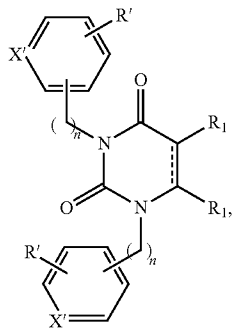

or Formula 4.1:

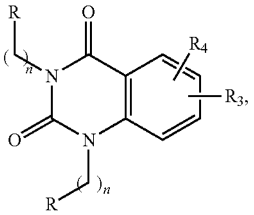

wherein:

each R is independently chosen from substituted or non-substituted $C_3$-$C_6$ cycloalkyl, substituted or non-substituted 5- to 6-membered heteroaryl, and substituted or non-substituted phenyl;

each $R_1$ is independently chosen from substituted and non-substituted $C_1$-$C_3$ alkyl;

$R_3$ is absent;

$R_4$ is hydrogen;

each R' is independently chosen from and $C_1$-$C_3$ alkyl, or R' is absent;

each X is independently N or CH;

------ represents a single or a double bond; and each n is 0 or 1.

2. The method of claim 1, wherein the compound of Formula 1D is

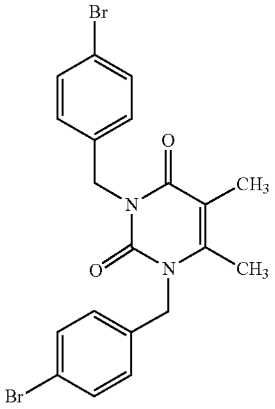 [SMILES: Cc1c(C)n(Cc2ccc(Br)cc2)c(=O)n(Cc2ccc(Br)cc2)c1=O]

or a pharmaceutically acceptable salt thereof.

3. The method of claim 1, wherein the compound of Formula 4.1 is

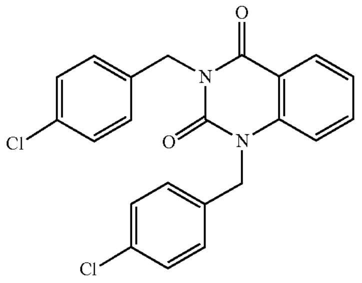 [SMILES: O=c1c2ccccc2n(Cc2ccc(Cl)cc2)c(=O)n1Cc1ccc(Cl)cc1]

or a pharmaceutically acceptable salt thereof.

4. A method for treating ApoL1 associated kidney disease comprising administering to a subject in need thereof a therapeutically effective amount of a compound or a pharmaceutically acceptable salt thereof, wherein the compound is

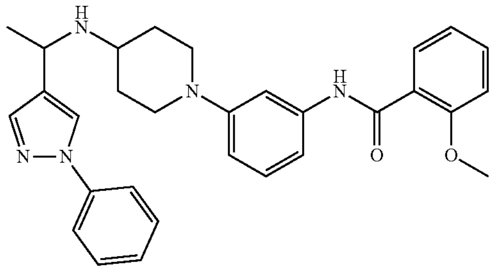.

5. A compound which is:

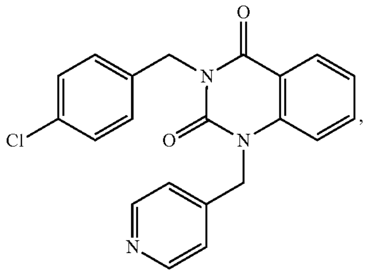,

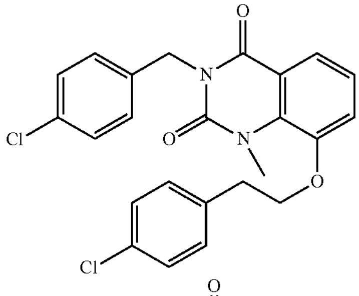,

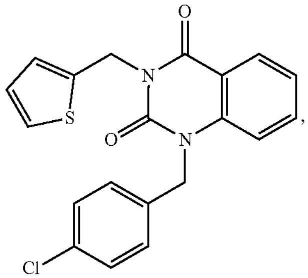,

-continued

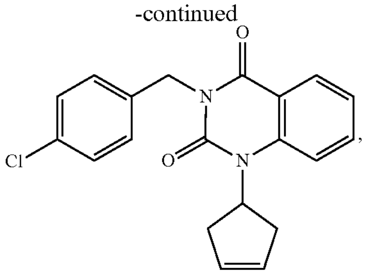,

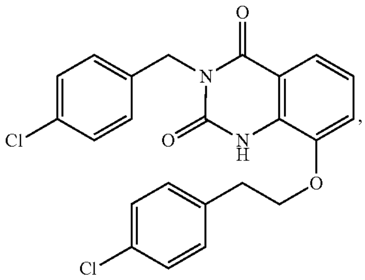,

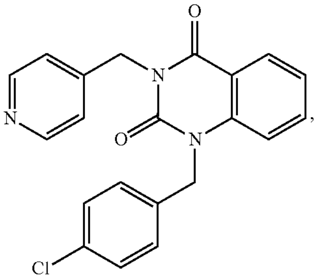,

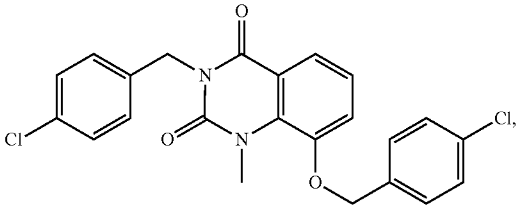,

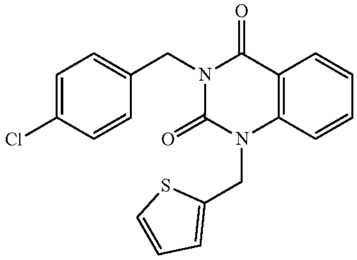,

-continued

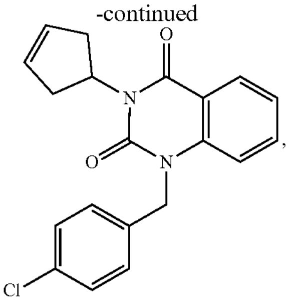,

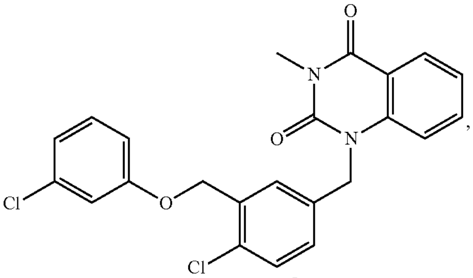,

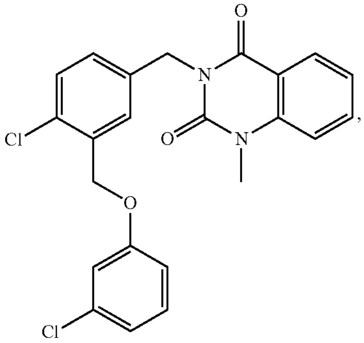, or a pharmaceutically acceptable salt thereof.

6. A pharmaceutical composition comprising (i) the compound of claim 5 or a pharmaceutically acceptable salt thereof, and (ii) a pharmaceutically acceptable carrier.

7. A method for treating ApoL1 associated kidney disease comprising administering to a subject in need thereof a therapeutically effective amount of the compound or a pharmaceutically acceptable salt according to claim 5.

* * * * *